(12) United States Patent
Wehrli et al.

(10) Patent No.: US 11,751,856 B2
(45) Date of Patent: Sep. 12, 2023

(54) COUPLING DEVICES FOR SURGICAL INSTRUMENTS AND RELATED METHODS

(71) Applicant: Medos International Sarl, Le Locle (CH)

(72) Inventors: Daniela Wehrli, Wangen bei Olten (CH); Philippe Lindenmann, Basel (CH)

(73) Assignee: Medos International Sarl, Le Locle (CH)

( * ) Notice: Subject to any disclaimer, the term of this patent is extended or adjusted under 35 U.S.C. 154(b) by 503 days.

(21) Appl. No.: 16/912,529

(22) Filed: Jun. 25, 2020

(65) Prior Publication Data

US 2020/0323521 A1   Oct. 15, 2020

Related U.S. Application Data

(63) Continuation of application No. 15/609,712, filed on May 31, 2017, now Pat. No. 10,722,223.

(51) Int. Cl.
*A61B 17/00* (2006.01)
*A61B 34/20* (2016.01)
(Continued)

(52) U.S. Cl.
CPC ............. *A61B 17/00* (2013.01); *A61B 34/20* (2016.02); *A61B 17/1671* (2013.01);
(Continued)

(58) Field of Classification Search
CPC ............... A61B 17/00; F16B 2/00; F16B 2/02
See application file for complete search history.

(56) References Cited

U.S. PATENT DOCUMENTS 3,251,605 A    5/1966   Ondeck
4,828,277 A    5/1989   De Bastiani et al.
(Continued)

FOREIGN PATENT DOCUMENTS

CN         1856277 A     11/2006
CN       104602618 B     11/2017
(Continued)

OTHER PUBLICATIONS

International Search Report and Written Opinion dated Oct. 10, 2018 for Application No. PCT/EP18/64251 (12 pages).
(Continued)

*Primary Examiner* — Andrew Yang
(74) *Attorney, Agent, or Firm* — Barnes & Thornburg LLP

(57) ABSTRACT

Coupling devices and related methods are disclosed herein, e.g., for coupling a surgical instrument to a navigation array or other component. The coupling device can reduce or eliminate movement between the instrument and the navigation array, improving navigation precision. The coupling device can be quick and easy to use, reducing or eliminating the need for extra steps or additional tools to attach or detach the instrument from the coupling device. In some embodiments, the single step of inserting an instrument into the coupling device can automatically lock the instrument within the coupling device in a toggle-free manner. The coupling device can include features for consistently attaching instruments thereto at a known or predetermined location and/or orientation.

20 Claims, 14 Drawing Sheets

(51) Int. Cl.
  *A61B 90/00* (2016.01)
  *A61B 17/16* (2006.01)
  *A61B 17/34* (2006.01)
  *A61B 17/70* (2006.01)
  *A61B 17/88* (2006.01)

(52) U.S. Cl.
  CPC ....... *A61B 17/3421* (2013.01); *A61B 17/7074* (2013.01); *A61B 17/8819* (2013.01); *A61B 2017/00455* (2013.01); *A61B 2017/00477* (2013.01); *A61B 2034/2048* (2016.02); *A61B 2034/2051* (2016.02); *A61B 2034/2055* (2016.02); *A61B 2090/034* (2016.02); *A61B 2090/363* (2016.02); *A61B 2090/3966* (2016.02); *A61B 2090/3979* (2016.02); *A61B 2090/3983* (2016.02)

(56) References Cited

U.S. PATENT DOCUMENTS

| | | |
|---|---|---|
| 5,211,576 A | 5/1993 | Tonkiss et al. |
| 6,190,395 B1 | 2/2001 | Williams |
| 6,270,087 B1 | 8/2001 | Mickel et al. |
| 6,434,507 B1 | 8/2002 | Clayton et al. |
| 6,530,579 B1 | 3/2003 | Houben et al. |
| 6,556,857 B1 | 4/2003 | Estes et al. |
| 6,932,823 B2 | 8/2005 | Grimm et al. |
| 7,043,961 B2 | 5/2006 | Pandey et al. |
| 7,153,308 B2 | 12/2006 | Peterson |
| 7,166,114 B2 | 1/2007 | Moctezuma De La Barrera et al. |
| 7,226,456 B2 | 6/2007 | O'Neil et al. |
| 7,274,958 B2 | 9/2007 | Jutras et al. |
| 7,289,227 B2 | 10/2007 | Smetak et al. |
| 7,314,048 B2 | 1/2008 | Couture et al. |
| 7,458,977 B2 | 12/2008 | McGinley et al. |
| 7,668,584 B2 | 2/2010 | Jansen |
| 7,688,998 B2 | 3/2010 | Tuma et al. |
| 7,873,400 B2 | 1/2011 | Moctezuma De La Barrera et al. |
| 7,877,890 B2 | 2/2011 | Weber |
| 7,993,353 B2 | 8/2011 | Roßner et al. |
| 8,216,211 B2 | 7/2012 | Mathis et al. |
| 8,303,596 B2 | 11/2012 | Plaßky et al. |
| 8,386,022 B2 | 2/2013 | Jutras et al. |
| 8,419,750 B2 | 4/2013 | Kienzle, III et al. |
| 8,509,878 B2 | 8/2013 | Pfeifer et al. |
| 8,560,047 B2 | 10/2013 | Haider et al. |
| 8,688,196 B2 | 4/2014 | Whitmore, III et al. |
| 8,734,432 B2 | 5/2014 | Tuma et al. |
| 8,764,025 B1 | 7/2014 | Gao |
| 8,800,939 B2 | 8/2014 | Karsak et al. |
| 8,821,511 B2 | 9/2014 | von Jako et al. |
| 8,834,455 B2 | 9/2014 | Kleven |
| 8,882,113 B2 | 11/2014 | Porter et al. |
| 8,961,500 B2 | 2/2015 | Dicorleto et al. |
| 8,961,536 B2 | 2/2015 | Nikou et al. |
| 8,985,593 B1 | 3/2015 | Gao |
| RE45,484 E | 4/2015 | Foley et al. |
| 9,005,211 B2 | 4/2015 | Brundobler et al. |
| 9,232,985 B2 | 1/2016 | Jacobsen et al. |
| 9,265,589 B2 | 2/2016 | Hartmann et al. |
| 9,873,155 B1 | 1/2018 | Wienhold |
| 10,722,223 B2 | 7/2020 | Wehrli et al. |
| 2004/0054489 A1 | 3/2004 | Moctezuma De La Barrera et al. |
| 2004/0077940 A1 | 4/2004 | Kienzle et al. |
| 2004/0138588 A1 | 7/2004 | Saikley |
| 2004/0171930 A1 | 9/2004 | Grimm et al. |
| 2005/0049485 A1 | 3/2005 | Harmon et al. |
| 2005/0124988 A1 | 6/2005 | Terrill-Grisoni et al. |
| 2005/0154296 A1 | 7/2005 | Lechner et al. |
| 2005/0203539 A1 | 9/2005 | Grimm et al. |
| 2006/0052691 A1 | 3/2006 | Hall et al. |
| 2007/0225725 A1 | 9/2007 | Heavener et al. |
| 2010/0160932 A1 | 6/2010 | Gschwandtner et al. |
| 2011/0263971 A1 | 10/2011 | Nikou et al. |
| 2012/0232377 A1 | 9/2012 | Nottmeier |
| 2013/0172907 A1 | 7/2013 | Harris |
| 2013/0178745 A1 | 7/2013 | Kyle, Jr. et al. |
| 2014/0257332 A1 | 9/2014 | Zastrozna |
| 2014/0276007 A1 | 9/2014 | Sela et al. |
| 2014/0371728 A1 | 12/2014 | Vaughn |
| 2015/0042052 A1 | 2/2015 | Furusawa et al. |
| 2015/0102567 A1 | 4/2015 | Chan |
| 2015/0182293 A1 | 7/2015 | Yang et al. |
| 2015/0265260 A1 | 9/2015 | Knodel et al. |
| 2015/0265769 A1 | 9/2015 | Bratbak et al. |
| 2015/0305817 A1 | 10/2015 | Kostrzewski |
| 2015/0362828 A1 | 12/2015 | Patel et al. |
| 2016/0015374 A1 | 1/2016 | Gifford et al. |
| 2016/0030076 A1 | 2/2016 | Faller et al. |
| 2016/0030129 A1 | 2/2016 | Christian et al. |
| 2017/0167514 A1* | 6/2017 | Reutter ................. A61B 90/39 |
| 2018/0008354 A1 | 1/2018 | Nguyen et al. |
| 2018/0344301 A1 | 12/2018 | Wehrli et al. |
| 2018/0344304 A1 | 12/2018 | Lindenmann et al. |

FOREIGN PATENT DOCUMENTS

| | | |
|---|---|---|
| CN | 103445828 B | 2/2018 |
| DE | 19636293 A1 | 3/1997 |
| EP | 1537829 A1 | 6/2005 |
| EP | 2540233 A1 | 1/2013 |
| EP | 2793728 A1 | 10/2014 |
| JP | 2014528763 A | 10/2014 |
| WO | 02/11620 A1 | 2/2002 |
| WO | 2013115640 A1 | 8/2013 |
| WO | 2014/003848 A1 | 1/2014 |
| WO | 2014198922 A1 | 12/2014 |
| WO | 2016023599 A1 | 2/2016 |

OTHER PUBLICATIONS

International Search Report and Written Opinion for Application No. PCT/EP2018/064268, dated Dec. 18, 2018 (19 pages).
International Preliminary Report on Patentability for Application No. PCT/EP2018/064268, dated Dec. 12, 2019 (14 pages).
U.S. Appl. No. 15/609,702, filed May 31 2017, Instrument Couplings and Related Methods.
U.S. Appl. No. 15/609,712, filed May 31 2017, Coupling Devices for Surgical Instruments and Related Methods.
Chinese Search Report for Application No. 201880035971, dated Aug. 30, 2022 (2 pages).
Japanese Office Action for Application No. 2019566154 dated May 27, 2022 (10 pages).

* cited by examiner

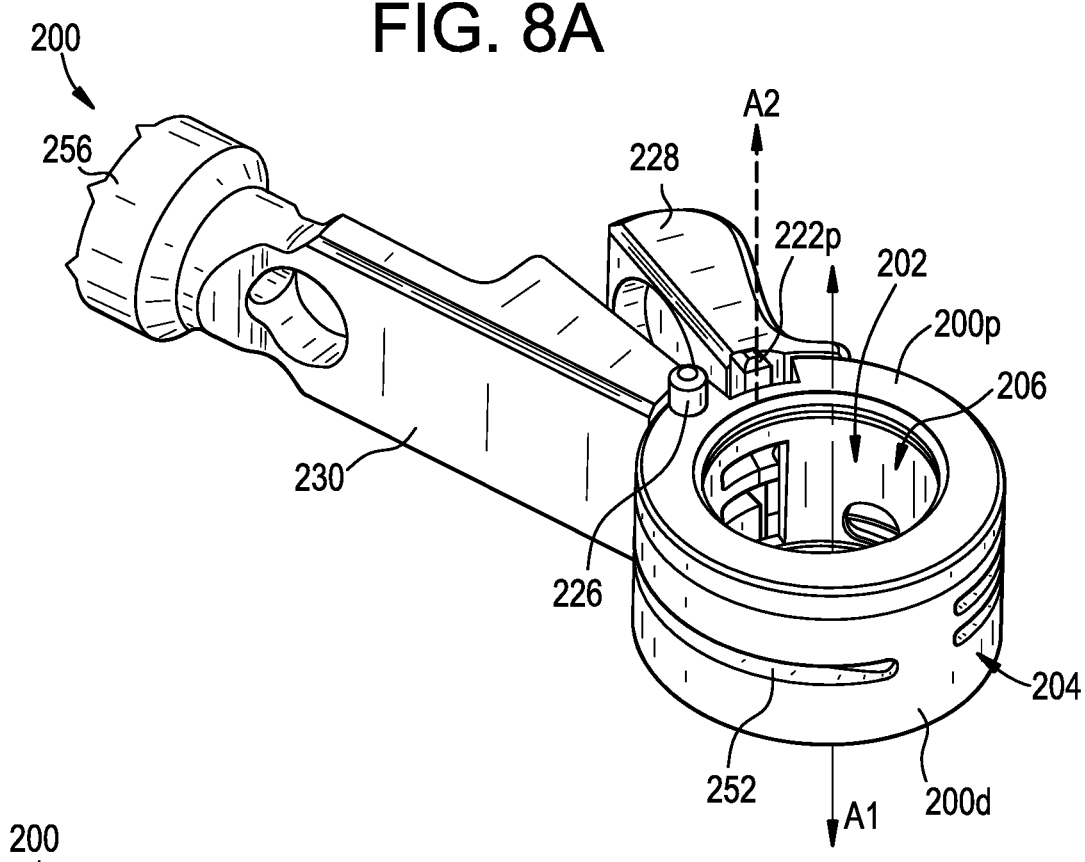
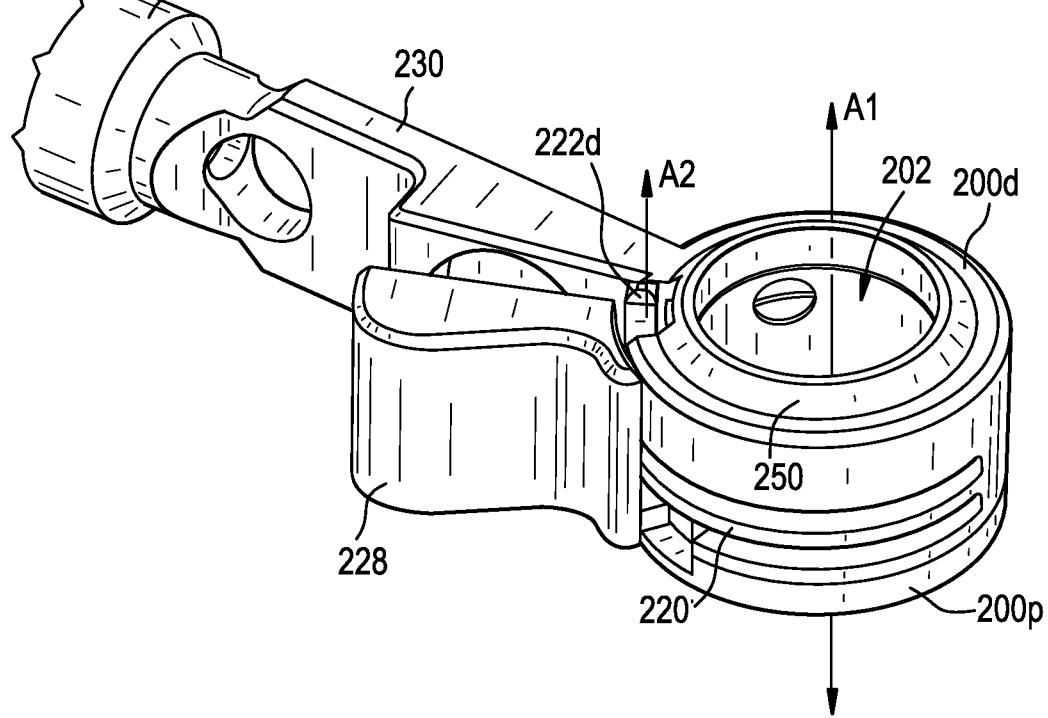

COUPLING DEVICES FOR SURGICAL INSTRUMENTS AND RELATED METHODS

CROSS-REFERENCE TO RELATED APPLICATIONS

This application is a continuation of U.S. application Ser. No. 15/609,712, filed May 31, 2017, which is hereby incorporated by reference in its entirety.

FIELD

Coupling devices for surgical instruments and related methods are disclosed herein, e.g., for coupling a surgical instrument to a navigation array or other component.

BACKGROUND

It is increasingly common for surgical procedures to involve navigation or tracking of instruments used during the surgery. Surgical navigation can be helpful in avoiding delicate neural or vascular structures when moving implants or instruments within a patient. In spinal surgery, for example, a surgical navigation system can be used during screw insertion, disc removal, bone preparation, and other steps of the surgery. Use of surgical navigation systems can also reduce the amount of X-ray exposure to which the patient and operating room staff are exposed.

A typical navigation system includes an array of markers attached to a surgical instrument, an imaging system that captures images of the surgical field, and a controller that detects the markers in the captured images and tracks movement of the markers within the surgical field. The controller associates a reference frame of the imaging system with a reference frame of the patient and, informed by a known geometry of the array and the instrument, determines how the instrument is being moved relative to the patient. Based on that determination, the controller provides navigation feedback to the surgeon.

The precision of the navigation system is strongly dependent on the design of the navigated instrument. When the navigation array is welded to the instrument or integrally-formed with the instrument, relatively high precision can be achieved. Such arrangements can be inconvenient, however, as the capability to remove the array from the instrument or to attach the array to other instruments is lacking. Further, arrangements having the navigation array integrally-formed with the instrument can require separate instruments for standard and navigation use, thereby raising costs for equipment.

A number of modular systems have been developed to allow the navigation array to be interchangeably attached with one or more instruments. These systems can be cumbersome to use, often requiring two hands, numerous steps, and/or additional tools to attach the array to the instrument and to remove the array from the instrument. These systems can also allow for considerable "play" between the instrument and the array, which can undesirably reduce the precision of the navigation. For example, toggling of the instrument relative to the array can introduce navigation error. Also, navigation error can be introduced if the array is not consistently attached to the instrument at a known or predetermined location and/or orientation.

SUMMARY

Coupling devices and related methods are disclosed herein, e.g., for coupling a surgical instrument to a navigation array or other component. The coupling device can reduce or eliminate movement between the instrument and the navigation array, improving navigation precision. The coupling device can be quick and easy to use, reducing or eliminating the need for extra steps or additional tools to attach or detach the instrument from the coupling device. In some embodiments, the single step of inserting an instrument into the coupling device can automatically lock the instrument within the coupling device in a toggle-free manner. The coupling device can include features for consistently attaching instruments thereto at a known or predetermined location and/or orientation.

In some embodiments, a coupling device can include a housing having proximal and distal ends and a central longitudinal axis A1 extending therebetween; and a clamp having a plurality of clamping elements and defining an instrument channel, the clamp being rotatable within the housing about the axis A1 between an unclamped position in which the clamping elements are free to move radially-outward away from the axis A1 and a clamped position in which the clamping elements are urged radially-inward towards the axis A1.

The coupling device can include a trigger movable relative to the housing between a first position in which the trigger maintains the clamp in the unclamped position and a second position in which the trigger allows the clamp to move to the clamped position. The trigger can be movable between the first and second positions by translating the trigger relative to the housing along an axis A2 that is parallel or substantially parallel to the axis A1. The trigger can include a rotation stop received within a slot formed in the clamp. The slot can include an axial portion in which the rotation stop cannot move laterally within the slot and a lateral portion in which the rotation stop is free to move laterally within the slot. The slot can include an axial portion in which the rotation stop cannot move laterally within the slot, the rotation stop being aligned with the axial portion when the trigger is in a resting position; a first lateral portion in which the rotation stop is free to move laterally within the slot, the rotation stop being aligned with the first lateral portion when the trigger is moved distally relative to the housing from the resting position, and a second lateral portion in which the rotation stop is free to move laterally within the slot, the rotation stop being aligned with the second lateral portion when the trigger is moved proximally relative to the housing from the resting position. The trigger can include an engagement feature that protrudes from one of the proximal and distal ends of the housing. The trigger can include a first engagement feature that protrudes from the proximal end of the housing and a second engagement feature that protrudes from the distal end of the housing. The first engagement feature can contact an instrument when the instrument is loaded into the proximal end of the housing. The second engagement feature can contact an instrument when the instrument is loaded into the distal end of the housing. Loading an instrument into the proximal end of the housing and loading an instrument into a distal end of the housing can both be effective to automatically actuate the trigger to release the clamp from the unclamped position. The trigger can be biased to the first position by a trigger spring. The trigger spring can include a flexible beam. Insertion of an instrument into the instrument channel can displace the trigger to the second position. The clamping elements can be urged radially-inward by an interior surface feature of the coupling device. The surface feature can include a ramped interior surface of the housing. The plurality of clamping elements can include a spherical ball or a wedge. The clamp can be biased towards the clamped position by a clamp spring. The housing and the clamp can each include handle levers movable towards one another to move the clamp to the unclamped position. The coupling device can include a navigation array attached to one of the handle levers. The coupling device can include a navigation array attached to the housing. The coupling device can include an orientation feature that prevents the trigger from being actuated by an instrument unless the orientation feature is aligned with a corresponding orientation feature of the instrument. The coupling device can include a conical ring-shaped projection extending from the housing and configured to be received within a corresponding recess of an instrument to ensure the device is coupled to the instrument in the correct orientation. The coupling device can include an instrument configured to be selectively attached to the coupling, the instrument including a groove that is engaged by the clamping elements when the instrument is received within the instrument channel. The coupling device can include an instrument configured to be selectively attached to the coupling, the instrument including a bearing surface that contacts the trigger and moves the trigger to the second position when the instrument is received within the instrument channel.

In some embodiments, a coupling device can include a housing having an instrument channel, a clamp, and a trigger; wherein insertion of an instrument into the instrument channel actuates the trigger to release the clamp, causing the clamp to rotate within the housing to clamp onto the instrument.

In some embodiments, a method of attaching an instrument to a coupling device can include inserting a portion of the instrument into an instrument channel of the coupling device, thereby displacing a trigger of the coupling device to release a clamp of the coupling device; and rotating the clamp within a housing of the coupling device to cause one or more clamping elements of the clamp to move radially-inward to clamp the instrument.

Said displacing of the trigger and said rotating of the clamp can occur automatically upon said insertion of the instrument. The instrument can be loaded into a proximal end of the coupling device to displace the trigger distally. The instrument can be loaded into a distal end of the coupling device to displace the trigger proximally. Displacing the trigger can include moving a rotation stop of the trigger out of an axial portion of a slot formed in the clamp and into a lateral portion of the slot. Rotating the clamp can include carrying the clamping elements across a surface feature of the housing to urge the clamping elements radially-inward. The trigger can be displaced relative to the housing along an axis that is parallel or substantially parallel to a central longitudinal axis of the instrument channel. Clamping the instrument can include radially centering the instrument in the instrument channel and translating the instrument axially within the instrument channel to urge an abutment surface of the instrument against a counterpart surface of the coupling device. An orientation feature of the coupling device can prevent the instrument from being inserted far enough into the coupling device to displace the trigger and release the clamp until the orientation feature of the coupling device is aligned with an orientation feature of the instrument. Displacing the trigger can load a flexible beam to which the trigger is mounted to bias the trigger against said displacement.

BRIEF DESCRIPTION OF THE DRAWINGS

The following detailed description is provided with the accompanying drawings, in which:

FIG. 8A is a perspective view of a coupling device;

FIG. 8B is another perspective view of the coupling device of FIG. 8A;

DETAILED DESCRIPTION

Figure 1:
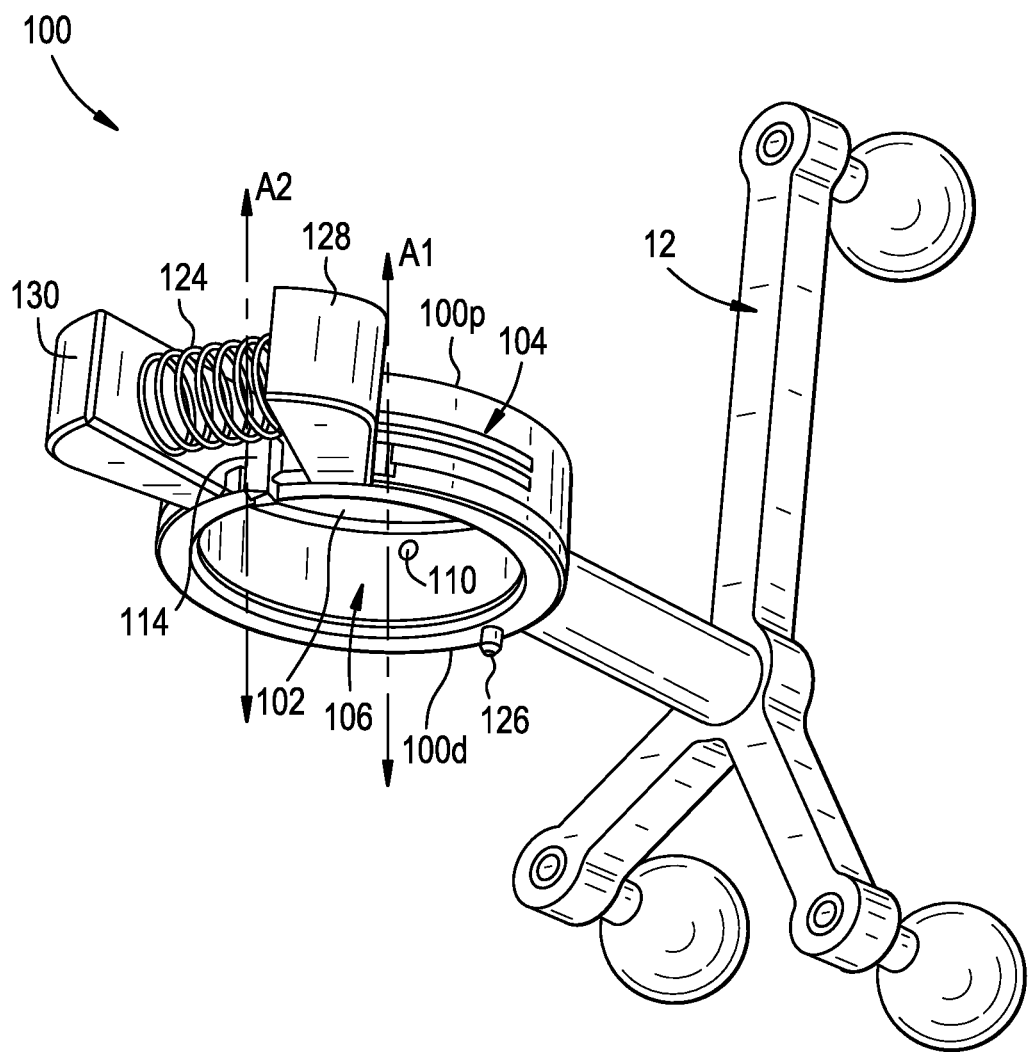
FIG. 1 is a perspective view of a coupling device having a navigation array attached thereto.

Coupling devices and related methods are disclosed herein, e.g., for coupling a surgical instrument to a navigation array or other component. The coupling device can reduce or eliminate movement between the instrument and the navigation array, improving navigation precision. The coupling device can be quick and easy to use, reducing or eliminating the need for extra steps or additional tools to attach or detach the instrument from the coupling device. In some embodiments, the single step of inserting an instrument into the coupling device can automatically lock the instrument within the coupling device in a toggle-free manner. The coupling device can include features for consistently attaching instruments thereto at a known or predetermined location and/or orientation.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1-4 illustrate an exemplary embodiment of a coupling device 100. The coupling device 100 can be used to attach an instrument to another instrument, object, or component. For example, the coupling device 100 can be used to attach a surgical instrument 10 to a navigation array 12. The coupling device 100 can define a channel 102 configured to receive at least a portion of an instrument therein. The channel 102 can extend from a proximal surface 100p of the coupling device 100 to a distal surface 100d of the coupling device.

The coupling device 100 can include a housing 104 in which a clamp 106 is disposed. The clamp 106 can be movable between an unclamped position and a clamped position. Rotation of the clamp 106 relative to the housing 104, e.g., about a central longitudinal axis A1 of the housing, can move the clamp between the unclamped position and the clamped position. The clamp 106 can include a clamping frame or ring 108 and one or more balls, wedges, spring arms, or other clamping elements 110. In the unclamped position, the clamp 106 can be positioned in a first rotational position relative to the housing 104 in which the clamping elements 110 are free to move radially-outward, away from the axis A1. In the clamped position, the clamp 106 can be positioned in a second rotational position relative to the housing 104 in which the clamping elements 110 are carried across a surface feature 112 of the housing. Movement of the clamping elements 110 across the surface feature 112 of the housing 104 can cause the clamping elements to move radially-inward towards the axis A1 to clamp onto an instrument inserted through the channel 102.

The coupling device 100 can include a trigger 114 for actuating the clamp 106. The trigger 114 can be configured to move relative to the housing 104, e.g., along an axis A2 that is parallel or substantially parallel to the axis A1. In a first position, the trigger 114 can interact with the clamp 106 via a rotation stop 116 and a slot 118 to hold the clamp in the unclamped position. In a second position, the trigger 114 can interact with the clamp 106 via the rotation stop 116 and the slot 118 to allow the clamp to move towards the clamped position. The trigger 114 can be biased towards the first position by a trigger spring 120.

The trigger 114 can be configured to actuate the clamp 106 automatically upon insertion of an instrument into the coupling device 100. The trigger 114 can include an engagement portion 122 configured to be pushed by an instrument as the instrument is inserted into the clamp 106, thereby moving the trigger to the second position described above to actuate the clamp.

The housing 104 and the clamp 106 can be biased to rotate with respect to one another by a bias element or clamp spring 124. For example, the clamp spring 124 can urge the clamp 106 towards the clamped position. The coupling device 100 can include an orientation feature or pin 126 for securing the coupling device in a specific rotational orientation relative to the instrument and/or to help prevent the coupling device from moving relative to the instrument.

The coupling device 100 can be movable between (i) an open position in which no instrument is received within the channel 102 and the coupling device is prepared to receive an instrument, and (ii) a closed position in which an instrument is received within the channel and is securely engaged by the coupling device to minimize or eliminate relative movement therebetween.

In the open position, as shown for example in FIGS. 6A-6D, the trigger 114 can be disposed in the first position described above, such that the rotation stop 116 is positioned in an axial portion 118A of the slot 118 to hold the clamp 106 in the unclamped position.

In the closed position, as shown for example in FIGS. 7A-7E, insertion of an instrument 10 into the channel 102 can displace the trigger 114 proximally against the bias of the trigger spring 120 to the second position described above. This movement of the trigger 114 can position the rotation stop 116 within a lateral portion 118B of the slot 118 in which the clamp 106 is free to rotate relative to the housing 104, at least to the degree permitted by the length of the lateral portion of the slot. Accordingly, this movement of the trigger 114 can release the clamp 106 to move towards the clamped position.

Referring again to FIGS. 1-4, to release the instrument 10 and return the coupling 100 to the open position, release levers 128, 130 of the clamp 106 and the housing 130 can be urged towards one another, e.g., by manual user input, to compress the clamp spring 124 and move the clamp to the unclamped position. This movement of the clamp 106 can also move the rotation stop 116 back into alignment with the axial portion 118A of the slot 118, allowing the trigger spring 120 to urge the trigger 114 back to the first position and once again hold the coupling device 100 in the open position.

The coupling device 100 can thus allow for quick and toggle-free connection to an instrument. In some embodiments, the single step of pushing the instrument into the coupling device 100 can automatically lock the instrument to the coupling device in a toggle-free manner, without requiring any additional steps or additional tools. Similarly, in some embodiments, the instrument can be released and the coupling device 100 can be reset in a single step, without requiring any additional steps or additional tools.

Figure 3:
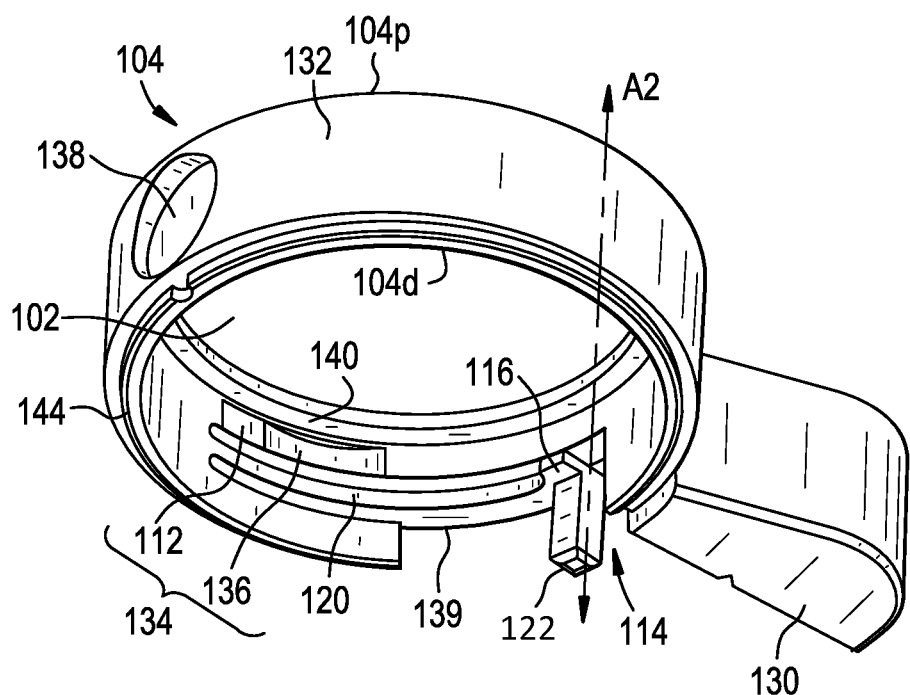
FIG. 3 is a perspective view of a housing of the coupling device of FIG. 1.

As shown in FIG. 3, the housing 104 can include a generally tubular or ring-shaped body defined by a sidewall 132 having a central opening 102. The opening 102 can extend along the axis A1 from a proximal surface 104p of the housing 104 to a distal surface 104d of the housing.

The housing 104 can have a circular shape, as shown, or can have various other shapes, such as oval, oblong, square, rectangular, triangular, and so forth. In some embodiments, the housing 104 can correspond with a shape of the clamp 106 disposed therein, or with a shape of a mating geometry of an instrument that is to be inserted therethrough. As described further below, the clamp 106 and/or the mating geometry can be inserted proximally or distally into the housing 104.

The housing 104 can include a lever or handle 130 extending therefrom. The handle 130 can be fixedly coupled to the housing 104 such that a force that is exerted on the handle can move the handle and the housing as a single unit. The handle 130 can allow a user to grasp the housing 104 and manipulate the orientation of the housing. The clamp spring 124 can bear against a spring seat defined by the handle 130.

The trigger 114 and the trigger spring 120 can be separate components mounted within the housing 104 or, as shown, can be formed integrally or monolithically with the housing. For example, the housing 104 can include first and second circumferential cut-outs that define a cantilevered beam 120 therebetween to form the trigger spring. By way of further example, the housing 104 can include first and second axial cut-outs that define a vertical post 114 to form the trigger. One or both of the axial cut-outs can define a relief area 139 to accommodate the handle 128 of the clamp 106 as the clamp rotates between the clamped and unclamped positions.

The trigger spring 120 can be configured to flex or bend to allow the trigger 114 to move along an axis A2 that is parallel or substantially parallel to the axis A1. It will be appreciated that although a cantilevered beam is shown in the illustrated embodiment, a leaf spring, coil spring, wave spring, non-cantilevered beam, or other bias element can be used for the trigger spring 120 instead or in addition.

The trigger 114 can extend from the trigger spring 120. The trigger 114 can be defined by one or more protrusions that extend from the trigger spring 120 towards the proximal surface 100p or the distal surface 100d of the coupling device 100. The trigger 114 can be an elongate square peg, as shown, or can take other forms, such as a button, a pin, a wedge, and the like. The trigger 114 can be formed integrally with the trigger spring 120 as shown, though the trigger can also be a separate component that is welded, threaded, glued, or otherwise coupled to the trigger spring. The trigger 114 can be positioned such that a force applied to the trigger can cause the trigger spring 120 to flex in a direction of the force. The trigger 114 can be located at a free terminal end of the trigger spring 120, as shown, or anywhere along the length of the trigger spring. The trigger 114 can include an engagement portion or surface 122 configured to contact and bear against an instrument as the instrument is inserted through the coupling device 100. The engagement portion 122 can protrude below the distal surface 100d of the coupling device 100 or, in the case of a proximally-oriented trigger 114, can protrude above the proximal surface 100p of the coupling device. In some embodiments, the engagement portion 122 can be aligned with, or depressed relative to, the proximal surface 100p or the distal surface 100d of the coupling device 100. In such embodiments, an instrument inserted through the coupling device 100 can include a protruding feature that contacts the engagement portion 122, e.g., a combination trigger-actuating protrusion and orientation feature.

The trigger 114 can include a rotation stop 116 formed thereon for interacting with the slot 118 of the clamp 106 to selectively prevent and allow relative rotation between the housing 104 and the clamp. For example, the rotation stop 116 can protrude radially-inward from the trigger 114 to engage a portion of the clamp 106. The rotation stop 116 can be located at a free terminal end of the trigger spring 120, as shown, or anywhere along the length of the trigger spring. The rotation stop 116 can exert a force on the clamp 106 to oppose a force exerted on the clamp by the clamp spring 124, as described further below.

The interior surface of the housing 104 can include surface features 112 for urging the clamping elements 110 of the clamp 106 radially-inward when the clamp rotates relative to the housing. In the illustrated embodiment, the interior surface of the housing 104 includes one or more cavities 134 spaced about the circumference of the housing. Each cavity 134 can include a relief portion 136 and a ramped, curved, stepped, or otherwise tapered portion 112. The relief portion 136 can have a radial depth sufficient to allow the clamping elements 110 of the clamp 106 to move radially-outward into the relief portion to disengage from an instrument disposed in the channel 102. The ramped portion 112 can have a radial depth that varies along a circumferential dimension of the ramped portion. The radial depth of a first end of the ramped portion 112 adjacent to the relief portion 136 can be greater than a radial depth of a second end of the ramped portion opposite from the relief portion. The radial depth of the ramped portion 112 can be less than the radial depth of the relief portion 136. When rotationally-aligned with the relief portions 136, the clamping elements 110 can be free to move radially-outward, e.g., to disengage from an instrument. When rotationally-aligned with the ramped portions 112, the clamping elements 110 can be urged radially-inward, e.g., to engage an instrument.

The navigation array 12 can be integrally formed with the housing 104 or can be attached thereto via various attachment mechanisms, such as a threaded, welded, snap-fit, interference, or other connection. For example, the housing 104 can include an interface 138 to which the navigation array 12 can be attached, e.g., in the form or a recess or pocket. The navigation array 12 can be attached to the housing 104 at a location opposite the handle lever 130 as shown, or at any other position along the housing. The navigation array 12 can be attached to the handle lever 130 of the housing 104.

The housing 104 can be configured to retain the clamp 106 within the housing. For example, the housing 104 can include a lip or shoulder 140 to limit proximal travel of the clamp 106 relative to the housing along the axis A1. As another example, the housing 104 can include a lid 142 to limit distal travel of the clamp 106 relative to the housing. The lid 142 can be formed as a ring shaped plate. The lid 142 can be selectively attached to the housing 104, e.g., during initial assembly of the coupling device 100, to retain the clamp 106 within the housing. The lid 142 can be attached to the housing 104 in various ways. For example, the housing 104 can include a ring-shaped, distally-extending mating feature 144 that engages a counterpart mating feature of the lid 142, e.g., via a snap-fit, interference fit, welded, or glued connection. The distal-facing surface of the lid 142 can include a window 146 through which the trigger 114 can protrude. The lateral sidewall of the lid 142 can include a relief to accommodate movement of the handle 128 of the clamp 106 as the clamp moves between the clamped and unclamped positions.

Figure 4:
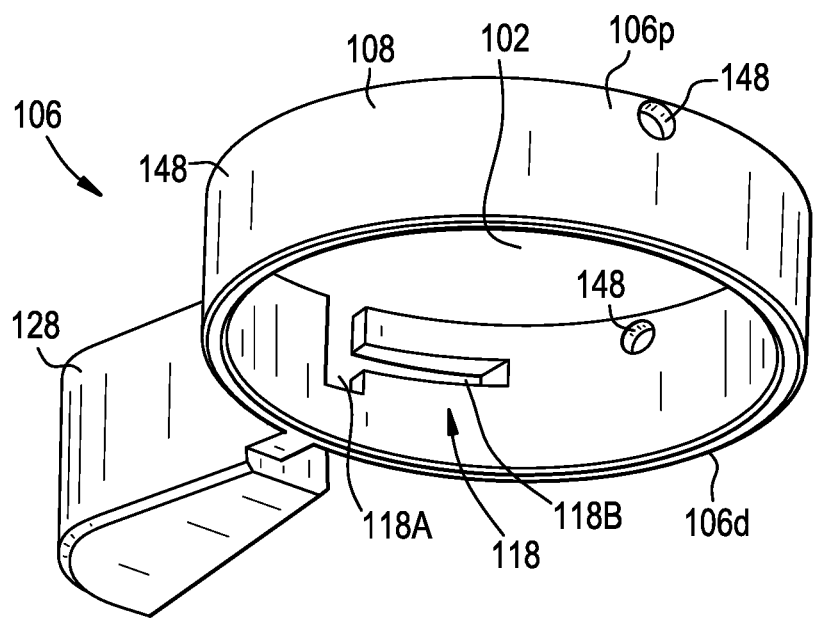
FIG. 4 is a perspective view of a clamp of the coupling device of FIG. 1.

As shown in FIG. 4, the clamp 106 can include a generally tubular or ring-shaped body defined by a sidewall 108 having a central opening 102. The opening 102 can extend along the axis A1 from a proximal surface 106p of the clamp 106 to a distal surface 106d of the clamp.

The clamp 106 can have a circular shape, as shown, or can have various other shapes, such as oval, oblong, square, rectangular, triangular, and so forth. In some embodiments, the clamp 106 can correspond with a shape of the housing 104 such that the clamp and the housing are concentric when the coupling device 100 is assembled. The clamp 106 can be shaped to receive a mating geometry of an instrument therethrough.

The clamp 106 can include a lever or handle 128 extending therefrom. The handle 128 can be fixedly coupled to the clamp 106 such that a force that is exerted on the handle 128 can move the handle and the clamp as a single unit. The handle 128 can allow a user to grasp the clamp 106 and manipulate the orientation of the clamp. The clamp spring 124 can bear against a spring seat defined by the handle 128.

The clamp 106 can include a slot 118 formed therein for interacting with the rotation stop 116 of the trigger 114 to selectively prevent and allow relative rotation between the housing 104 and the clamp. The slot 118 can include an axial portion 118A that extends in a proximal-distal direction that is parallel to the axis A1. The circumferential dimension of the axial portion 118A can be substantially equal to a corresponding dimension of the rotation stop 116, such that when the rotation stop is positioned within the axial portion of the slot, the clamp 106 is constrained from rotating relative to the housing 104 about the axis A1. The slot 118 can include a lateral portion 118B that extends perpendicular or substantially perpendicular to the axial portion 118A. The circumferential dimension of the lateral portion 118B can be greater than a corresponding dimension of the rotation stop 116, such that when the rotation stop is positioned within the lateral portion of the slot, the rotation stop can slide within the slot and the clamp 106 is free to rotate relative to the housing 104 about the axis A1, at least to the degree permitted by the length of the slot and/or to the degree permitted by the housing geometry or before the instrument is clamped.

The clamp 106 can include one or more openings or throughholes 148 spaced about the circumference of the clamp through which the clamping elements 110 can protrude to engage an instrument disposed within the clamp. The openings 148 can be sized and shaped to allow the clamping elements 110 to protrude through the openings while still retaining the clamping elements between the clamp 106 and the housing 104. For example, the openings 148 can be circular and can have a diameter that is less than a diameter of the clamping elements 110. The openings 148 can also be sized and shaped such that the clamping elements 110 rotate with the clamp 106 when the clamp rotates relative to the housing 104 about the axis A1. For example, the openings 148 can have a circumferential dimension small enough to ensure that the clamp 106 carries the clamping elements 110 across the surface features 112 of the housing 104 when the clamp is rotated relative to the housing.

The clamp 106 can include one or more clamping elements 110 configured to move radially-inward or radially-outward in response to rotational movement of the clamp within the housing 104. For example, the clamp 106 can include a plurality of spherical balls 110 mounted within the openings 148 of the clamp. While spherical balls 110 are shown, it will be appreciated that any of a variety of clamping elements can be used instead or in addition, such as wedges, rollers, chucks, spring fingers, fins, and so forth. The illustrated clamp 106 includes three clamping elements 110 spaced equally about the circumference of the clamp. In other arrangements, the clamp 106 can include a greater or lesser number of clamping elements 110, and/or clamping elements spaced in other positions.

The clamp spring or other bias element 124 can be disposed between the housing 104 and the clamp 106 to bias the clamp towards the clamped position. For example, the bias element 124 can disposed between the respective handle levers 128, 130 of the clamp 106 and the housing 104. While a coil spring 124 is shown, it will be appreciated that various other bias elements can be used instead or in addition, such as leaf springs, wave springs, torsion springs, resilient compressible members, etc.

The coupling device 100 can include an orientation feature configured to engage a corresponding orientation feature of an instrument to allow the coupling device to be attached to the instrument in a known or predetermined rotational position. This can be particularly useful when navigating asymmetrical instruments. For example, the coupling device 100 can include an orientation feature in the form of a pin 126 that projects from a proximal or distal surface of the coupling device. The orientation pin 126 can be received within a corresponding orientation feature of an instrument, e.g., a recess of the instrument, to allow for a specific orientation of the coupling device 100 relative to the instrument to be quickly and repeatedly achieved. The orientation feature 126 can be formed integrally with the housing 104 or the lid 142, or can be a separate component attached thereto. The orientation feature 126 can project distally below the distal surface 100d of the coupling device 100, such that interference between the orientation feature and an instrument prevents the instrument from advancing far enough proximally into the coupling device to actuate the trigger 114, unless the orientation feature is aligned with a corresponding orientation feature of the instrument. While a cylindrical pin 126 is shown, the orientation feature can also be formed as a wedge, bolt, or other stationary projection. Although a single orientation feature 126 is shown, the coupling device 100 can include a plurality of orientation features.

As noted above, the coupling device 100 can be used to attach an instrument to a navigation array. The navigation array can be attached to and can extend from the housing 104, the clamp 106, the handles 128, 130, or any other portion of the coupling device 100. The coupling device 100 and the navigation array can be a single monolithic unit, or can be separate components permanently or temporarily joined to one another. For example, the navigation array can be rigidly attached, e.g., welded or permanently affixed, to the coupling device 100 during manufacturing via a shaft, as shown in the illustrated embodiment, or can be selectively coupled to the coupling device via a mating interface such as a threaded, snap-fit, or interference-fit connection. The navigation array can be attached to the coupling device 100 via a jointed connection, such that the navigation array is adjustable in one or more degrees of freedom with respect to the coupling device.

While a single navigation array 12 is shown, the coupling device 100 can include multiple arrays, e.g., one at each end. Use of multiple navigation arrays can improve tracking accuracy, field of view, or redundancy. The navigation array 12 can be detected by a navigation system, can communicate with the navigation system, or can be otherwise operably coupled to the navigation system to allow the position and/or orientation of the coupling device 100 and an instrument received therein to be registered with and tracked by the navigation system.

Figure 2:
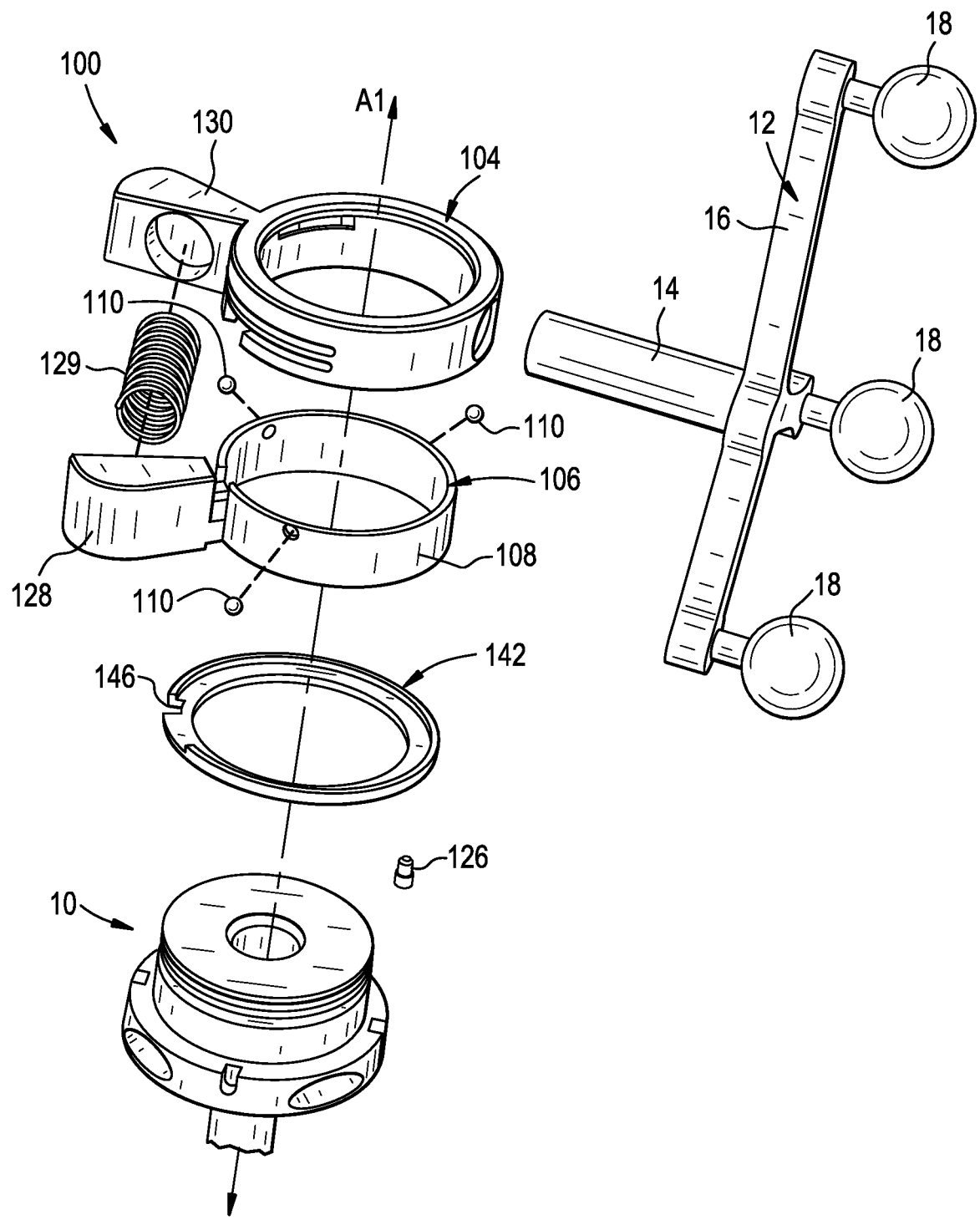
FIG. 2 is an exploded perspective view of the coupling device of FIG. 1, shown with a navigation array and an instrument.

The navigation array 12 can be attached to the coupling device 100 such that a position and orientation of the coupling device with respect to the navigation array 12 is known. It will be appreciated that the structure and operation of the navigation array 12 can vary depending on the type of navigation system used. FIG. 2 illustrates an exemplary navigation array 12 that includes a cylindrical shaft 14 that attaches a frame 16 of the navigation array to the coupling device 100. The frame 16 includes three arms, each arm having a sphere-shaped fiducial 18 attached thereto for use with an optical navigation system. The fiducials 18 can be arranged in predetermined positions and orientations with respect to one another. The fiducials 18 can be positioned within a field of view of the navigation system and can be identified in images captured by the navigation system. Exemplary fiducials 18 include infrared reflectors, LEDs, and so forth. The navigation array 12 can be or can include an inertial measurement unit (IMU), an accelerometer, a gyroscope, a magnetometer, other sensors, or combinations thereof. The sensors can transmit position and/or orientation information to the navigation system, e.g., to a processing unit of the navigation system.

Figure 5A:
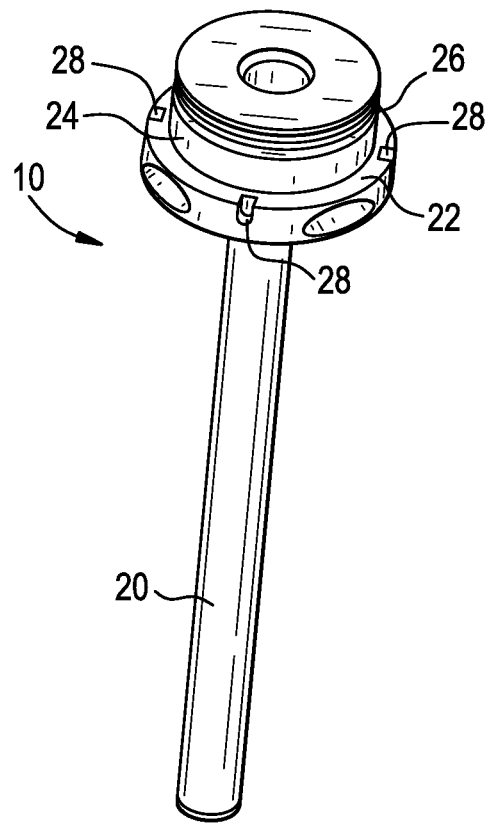
FIG. 5A is a perspective view of an instrument that can be used with the coupling device of FIG. 1.
Figure 5B:
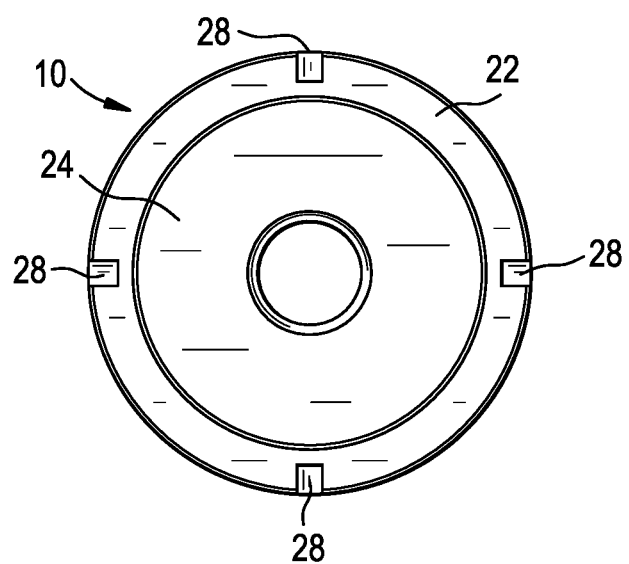
FIG. 5B is a top view of the instrument of FIG. 5A.
Figure 6A:
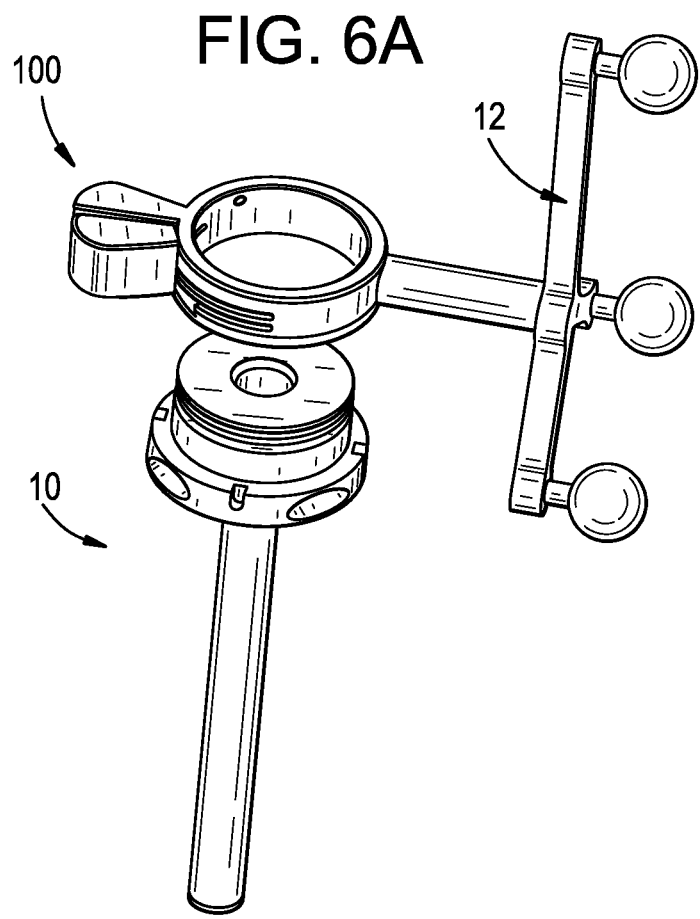
FIG. 6A is a perspective view of an instrument being loaded into the coupling device of FIG. 1.
Figure 6B:
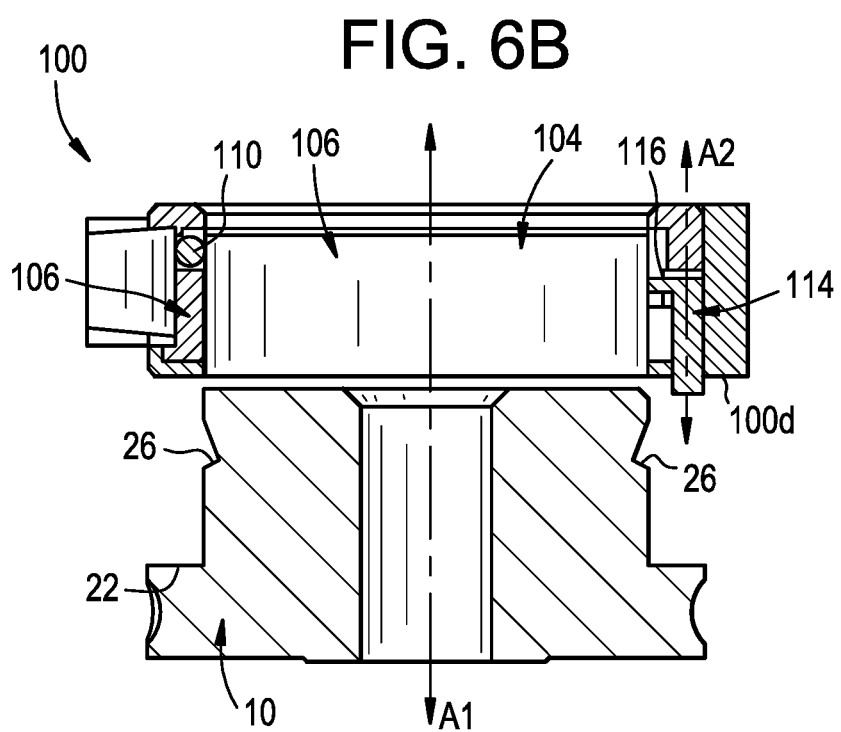
FIG. 6B is a sectional side view of an instrument being loaded into the coupling device of FIG. 1.
Figure 6C:
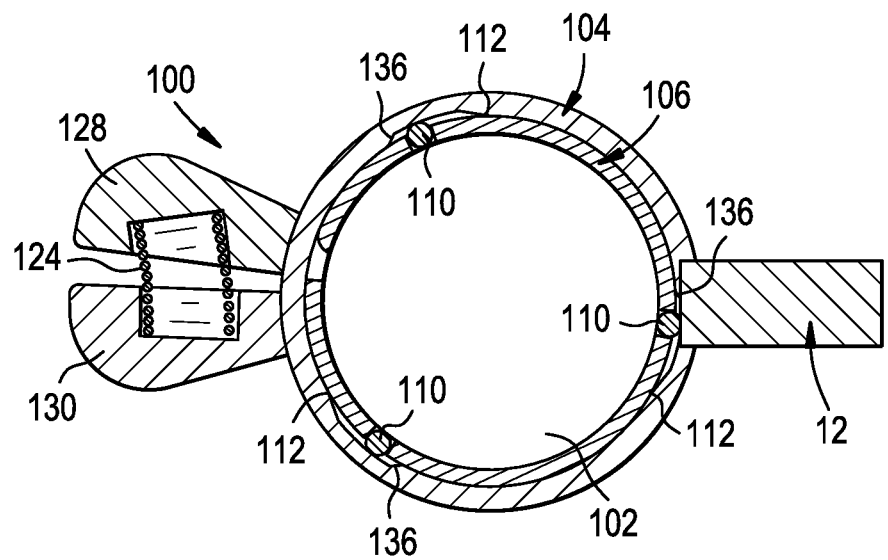
FIG. 6C is a sectional top view of the coupling device of FIG. 1, shown in an open position.
Figure 6D:
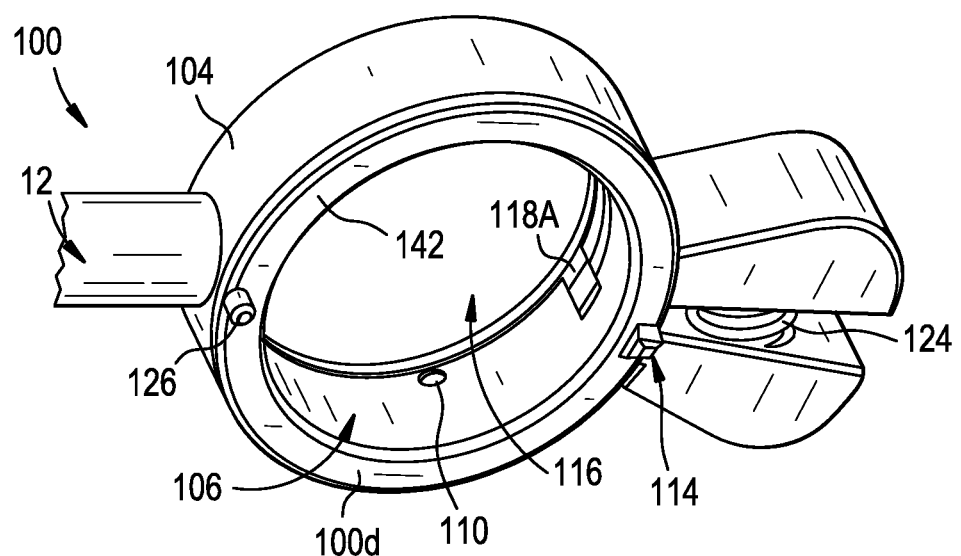
FIG. 6D is a perspective view of the coupling device of FIG. 1, schematically illustrating movement of a trigger upon instrument insertion.
Figure 7A:
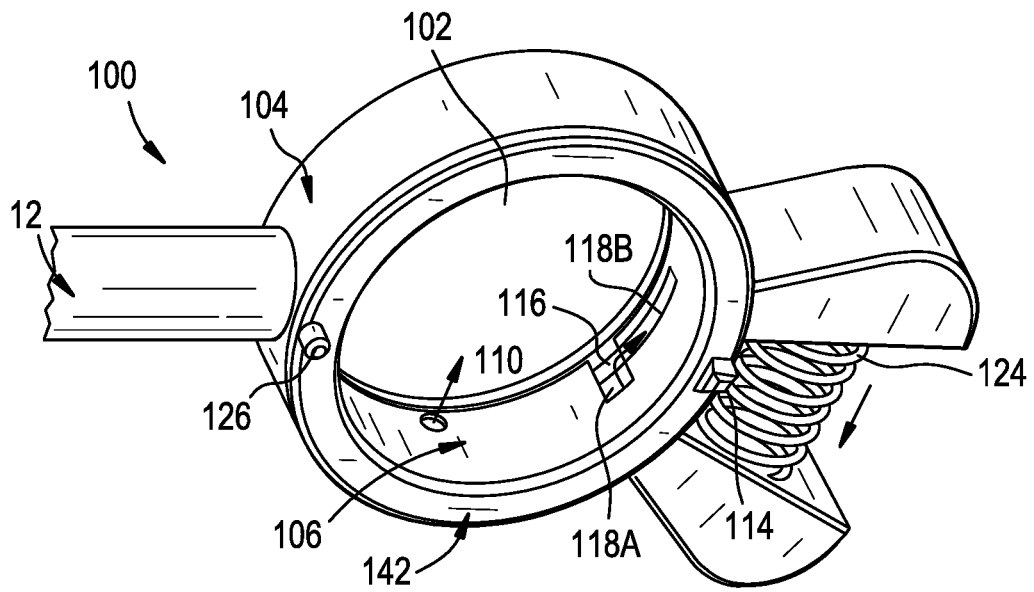
FIG. 7A is a perspective view of the coupling device of FIG. 1, schematically illustrating movement of a clamp upon instrument insertion.
Figure 7B:
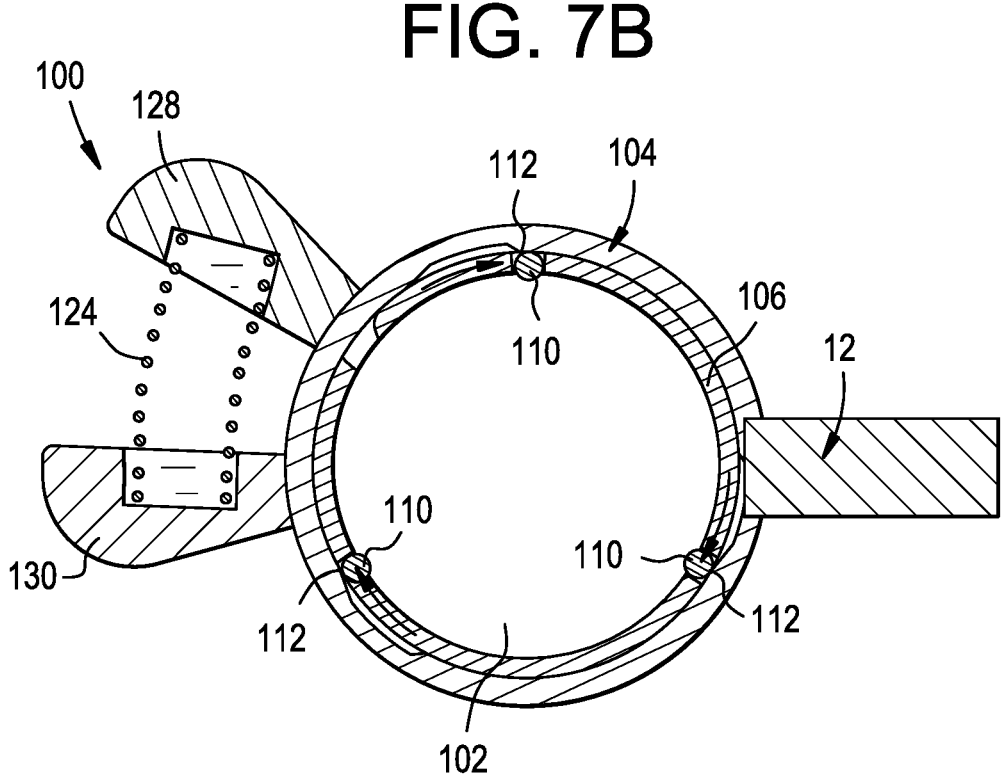
FIG. 7B is a sectional top view of the coupling device of FIG. 1, shown in a closed position.
Figure 7C:
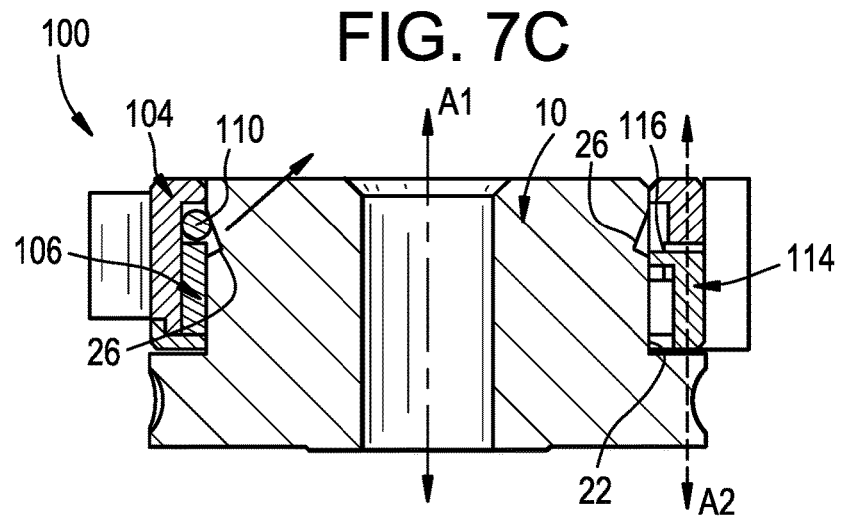
FIG. 7C is a sectional side view of the coupling device of FIG. 1, shown with an instrument inserted therethrough.
Figure 7D:
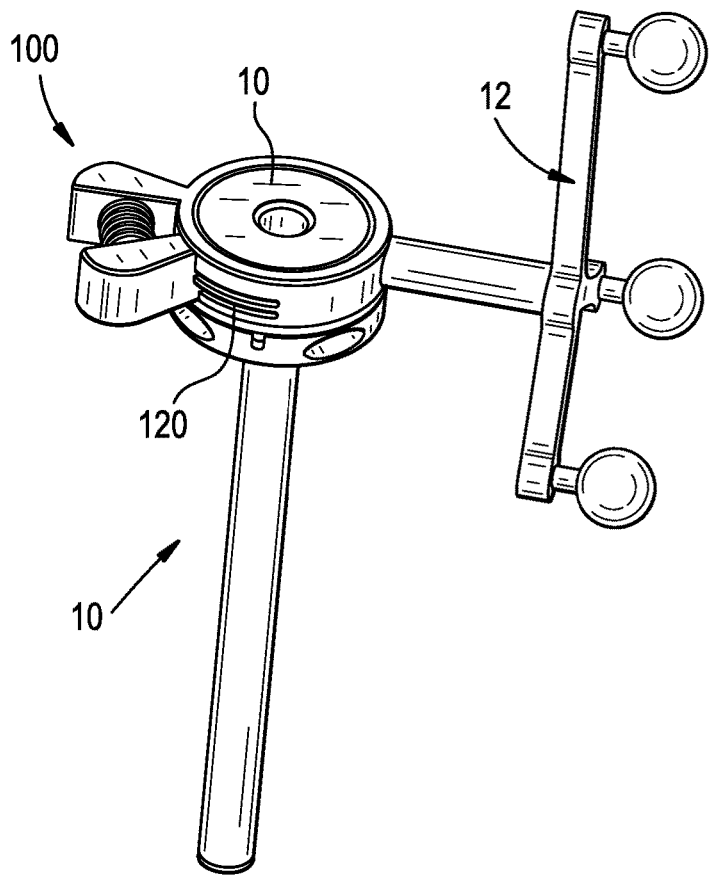
FIG. 7D is a perspective view of the instrument and coupling device of FIG. 7C.
Figure 7E:
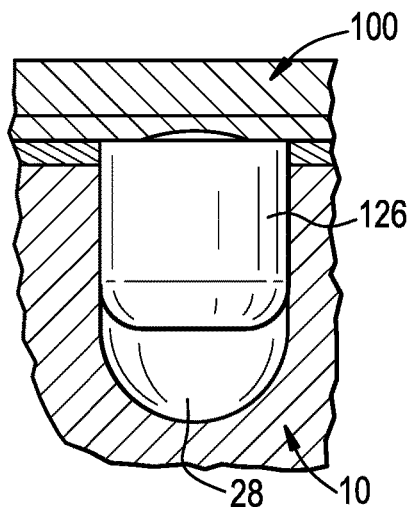
FIG. 7E is a detail sectional view of an orientation feature of the coupling device of FIG. 1 received within an orientation feature of an instrument.

The coupling device 100 can be used with any of a variety of instruments. In some embodiments, one or more instruments can include a mating geometry designed to operate with the coupling device 100. An exemplary instrument mating geometry is shown in FIGS. 5A-5B. It will be appreciated that the illustrated geometry is exemplary and that the coupling device 100 can be used with any of a variety of instruments having any of a variety of mating geometries. In some embodiments, the mating geometry of the instrument can be a cylindrical shaft. In some embodiments, the mating geometry of the instrument can be a cylindrical shaft with an annular groove formed therein.

The instrument 10 can include a generally cylindrical shaft 20 with a mating geometry at or near the proximal end of the shaft. The distal end of the shaft can include the functional operating features of the instrument 10, such as an end effector, blade, rasp, etc. Alternatively, as shown, the instrument 10 can be a guide tube configured to receive one or more other instruments therethrough. The instrument shaft 20 can be cannulated, e.g., to allow the instrument to be inserted over a guidewire or to allow instruments, cement, or other flowable materials to be delivered through the instrument 10. By navigating the instrument 10, indirect navigation of another instrument or tool inserted therethrough can be achieved.

The mating geometry can include a shoulder or other abutment surface 22 configured to contact the trigger 114 as the instrument 10 is inserted into the coupling device 100 to release the clamp 106. The illustrated mating geometry is designed to be loaded into a distal end of the coupling device 100, and therefore includes a proximal-facing shoulder 22 for contacting a trigger 114 extending distally from the coupling device during said insertion. It will be appreciated that the mating geometry can alternatively or additionally be designed to be loaded into a proximal end of the coupling device 100, in which case the mating geometry can include a distal-facing shoulder for contacting a trigger extending proximally from the coupling device during said insertion.

The mating geometry can include a section 24 of the instrument shaft 20 having a diameter sized to match or substantially match the diameter of the channel 102 of the coupling device. The coupling device 100 can be operable with instruments having any of a variety of diameters. For example, the channel 102 of the coupling device can have a diameter in the range of about 10 mm to about 32 mm, about 10 mm to about 28 mm, and/or about 10 mm to about 22 mm. The coupling device 100 can be configured to securely clamp onto multiple different instruments having different diameters. For example, the clamping elements 110 of the coupling device 100 can have a radial range of motion sufficient to take up any gap between an outer surface of the instrument and an inner surface of the clamp 106, such that the coupling device can support a range of instrument diameters, including instrument diameters that are less than the diameter of the clamp.

The mating geometry can include a section of the instrument shaft 20 in which a groove 26 is formed in the outer surface of the instrument 10. The groove 26 can receive the clamping elements 110 of the coupling device 100 when the instrument 10 is clamped within the coupling device. The groove 26 can interact with the clamping elements 110 to limit or prevent axial translation of the instrument 10 relative to the coupling device 100 along the axis A1. The proximal and/or distal surfaces of the groove 26 can be ramped, curved, stepped, or otherwise tapered, such that pressing the clamping elements 110 against the groove 26 can push or pull the instrument axially within the coupling device 100. Such axial movement can help ensure that the coupling device 100 is attached at a known axial location along the instrument 10, and can ensure that the shoulder 22 of the instrument is pulled into engagement with the trigger 114 during insertion of the instrument. The clamping elements 110 can apply a radially-directed force to the groove 26 to center the instrument 10 radially within the coupling device 100. The clamping elements 110 can apply a radially-directed force to the groove 26 to frictionally engage the instrument 10 and thereby limit or prevent rotation of the instrument relative to the coupling device 100 about the axis A1. In other arrangements, the clamping elements 110 can engage the instrument 10 without limiting or preventing rotation.

The mating geometry can include one or more orientation features for interacting with the orientation features of the coupling device 100. For example, the mating geometry can include one or more recesses or slots 28 configured to receive the orientation pin 126 of the coupling device 100. As shown in FIG. 5B, the mating geometry can include four recesses 28 spaced equally about the circumference of the instrument 10, though it will be appreciated that the instrument can include any number of recesses disposed in any of a variety of positions about the instrument. The number of recesses 28 can define the number of discrete rotational positions about the axis A1 at which the instrument 10 can be attached to the coupling device 100. The orientation recesses 28 can be formed in the abutment surface 22 of the instrument 10 as shown, or in any other portion of the instrument.

In use, the coupling device 100 can be used to attach an instrument 10 to another instrument, object, or component. For example, the coupling device 100 can be used to attach an instrument 10 to a navigation array 12.

The coupling device 100 can be movable between (i) an open position in which no instrument is received within the channel 102 and the coupling device is prepared to receive an instrument, and (ii) a closed position in which an instrument is received within the channel and is securely engaged by the coupling device to minimize or eliminate relative movement therebetween.

FIGS. 6A-6D illustrate the coupling device 10 in the open position. As shown, the trigger 114 can be in the first position, in which the trigger protrudes from a distal surface 100*d* of the coupling device 100 and in which the rotation stop 116 of the trigger is positioned in the axial portion 118A of the clamp slot. With the rotation stop 116 positioned in the axial portion 118A of the slot, rotation of the clamp 106 about the axis A1 can be prevented, thereby maintaining the clamp in the unclamped position. The trigger 114 can be maintained in the axial portion 118A of the clamp slot by the bias of the trigger spring 120. In the unclamped position of the clamp 106, the clamping elements 110 can be aligned with the relief portions 136 of the cavities 134 formed in the housing 104, such that the clamping elements are free to move radially-outward away from the axis A1. For example, insertion of an instrument 10 into the coupling device 100 with the clamp 106 in this position can cause the clamping elements 110 to retreat into the relief portions 136 of the cavities 134. In the unclamped position, the clamp spring 124 can be compressed between the levers 128, 130 of the clamp 106 and the housing 104.

FIGS. 7A-7E illustrate the coupling device 100 in the closed position. As shown, insertion of an instrument 10 into the channel 102 can displace the trigger 114 proximally to the second position, loading the trigger spring 120 and moving the rotation stop 116 along the axis A2 to position the rotation stop in alignment with the lateral portion 118B of the slot. With the rotation stop 116 no longer engaged with the axial portion 118A of the slot, the clamp 106 can be released to rotate relative to the housing 104 about the axis A1. The bias force supplied by the clamp spring 124 can urge the clamp 106 to rotate towards the clamped position, thereby guiding the clamping elements 110 along the ramped portions 112 of the cavities 134 to move the clamping elements radially inward into firm engagement with the instrument 10. The rotation stop 116 can travel along the lateral portion 118B of the clamp slot to allow the clamp 106 to continue rotating to the extent needed to clamp the instrument 10. In particular, the clamp 106 can continue to rotate relative to the housing 104 until the clamping elements 110 are firmly wedged between the instrument 10 and the ramped portions 112 of the cavities 134. As noted above, where an orientation feature 126 is included, displacement of the trigger 114 during insertion of an instrument 10 can be prevented by interference between the orientation feature and the instrument, until the orientation feature is aligned with a corresponding orientation feature 28 of the instrument. In the example above, the trigger 114 is actuated automatically by engagement with the instrument 10 during instrument insertion. In other arrangements, the trigger 114 can be manually actuated by a user. For example, the trigger 114 can be actuated by a button, lever, or other control.

In the closed position, the clamping elements 110 can be received within the groove 26 of the instrument 10 to limit or prevent translation of the instrument along the axis A1 relative to the coupling device 100, e.g., limiting or preventing surging movement, and/or to limit or prevent rotation of the instrument 10 about the axis A1 relative to the coupling device 100, e.g., limiting or preventing roll movement. Also in the closed position, the clamping elements 110 can be wedged against the exterior surface of the instrument 10 to limit or prevent lateral translation of the instrument relative to the coupling device 100 and/or to limit or prevent pivoting movement of the instrument relative to the coupling device 100, e.g., limiting or preventing heaving, swaying, pitching, and/or yawing movement. The coupling device 100 can thus limit or prevent movement of the instrument 10 relative to the coupling device in at least six degrees of freedom. It will be appreciated that, in some embodiments, the coupling device 100 can be configured to preserve one or more of these degrees of freedom.

In the closed position, the clamping elements 110 can be received within the groove 26 of the instrument 10 to center the instrument radially within the coupling device 100. In the closed position, the clamping elements 110 can be received within the groove 26 of the instrument 10 to urge the instrument axially along the axis A1 relative to the coupling device 100 to ensure that the instrument displaces the trigger 114 far enough to release the clamp 106 and/or to ensure that the instrument is clamped at a known or predetermined axial position relative to the coupling device.

To release the instrument 10 and return the coupling device 100 to the open position, the handle levers 128, 130 can be squeezed together, e.g., by manual user input, to rotate the clamp 106 back towards the unclamped position, compressing the clamp spring 124. With the clamping elements 110 now offset from the ramped portions 112 of the cavities 134, the clamping elements can be free to move radially-outward to disengage from the instrument 10. As the clamp 106 rotates relative to the housing 104, the rotation stop 116 can travel along the lateral portion 118B of the slot 118 until it is aligned with the axial portion 118A of the slot, at which point the bias force of the trigger spring 120 can urge the rotation stop back into the axial portion of the slot. When the user-applied force is removed from the handle levers 128, 130, the rotation stop 116 can remain within the axial portion 118A of the slot, holding the coupling device 100 in the open position described above such that the coupling device is ready to be coupled to an instrument 10.

The coupling device 100 can be configured such that an instrument can be loaded into a proximal end of the coupling device, into a distal end of the coupling device, or into either a proximal or a distal end of the coupling device.

The instrument and/or the coupling device 100 can be specifically designed for distal loading. For example, as shown, the trigger 114 and the orientation feature 126 can project from a distal-facing surface 100d of the coupling device 100. As also shown, the mating geometry of the instrument 10 can include a proximal-facing abutment surface 22 for contacting the trigger 114 during loading, can include proximal-facing orientation features 28, and/or can include a mating groove 26 positioned proximal to the abutment surface.

The instrument and/or the coupling device 100 can be specifically designed for proximal loading. For example, the trigger 114 and the orientation feature 126 can project from a proximal-facing surface 100p of the coupling device 100. The mating geometry of the instrument 10 can include a distal-facing abutment surface 22 for contacting the trigger 114 during loading, can include distal-facing orientation features 28, and/or can include a mating groove 26 positioned distal to the abutment surface.

The instrument and/or the coupling device 100 can be designed to support both proximal and distal loading. FIGS. 8A-12B illustrate an exemplary coupling device 200 that can support both proximal and distal loading. Except as indicated below and as will be readily appreciated by one having ordinary skill in the art in view of the present disclosure, the structure and function of the device 200 is substantially the same as that of the device 100 described above, and therefore a detailed description is omitted here for the sake of brevity.

For example, the coupling device 200 can include a central longitudinal axis A1, an instrument channel 202, a housing 204 with ramped surface features 212, a clamp 206 biased by a clamp spring 224 and having a slot 218, one or more clamping elements 210, a trigger 214 with a rotation stop 216 and biased by a trigger spring 220, a clamp handle 228, a housing handle 230, and/or an orientation feature 226, all being substantially of the type described above.

Figure 9A:
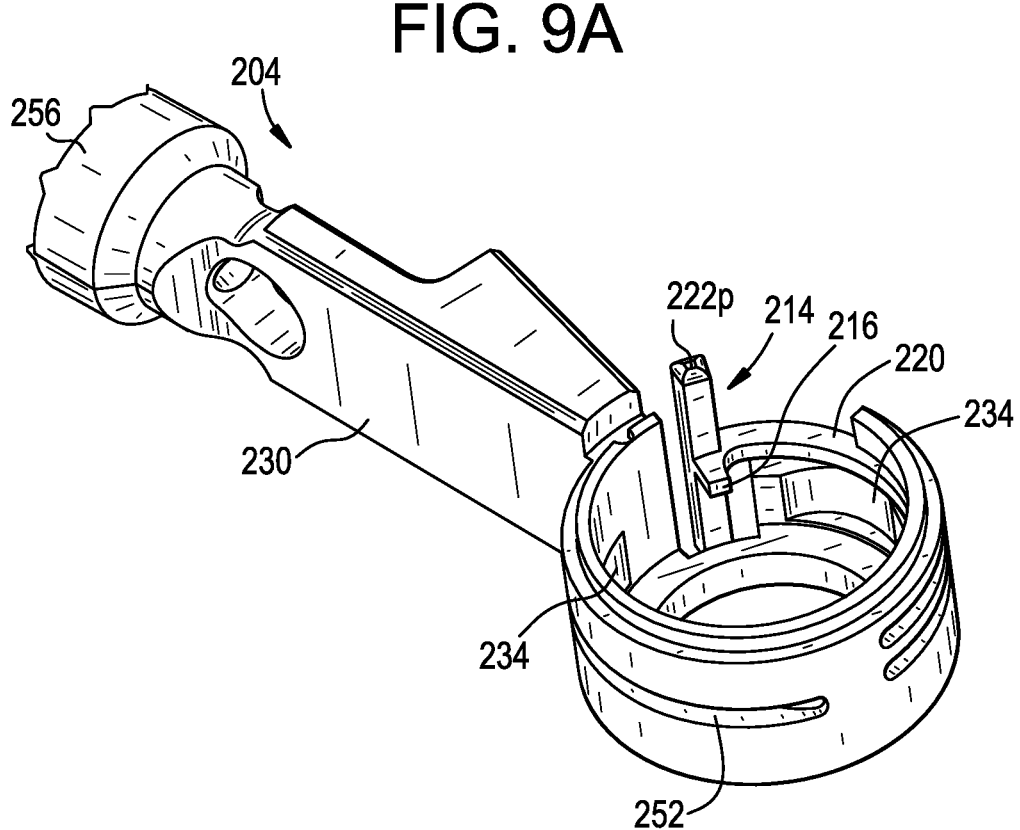
FIG. 9A is a perspective view of a housing of the coupling device of FIG. 8A.
Figure 9B:
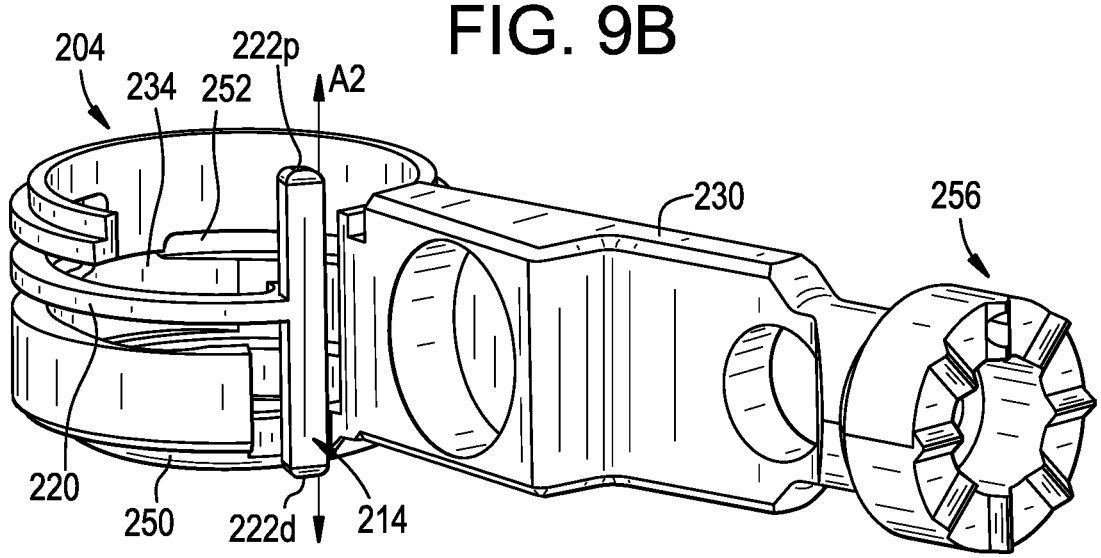
FIG. 9B is another perspective view of the housing of FIG. 9A.

The coupling device 200 can include a multi-directional trigger 214. For example, a first engagement portion 222p of the trigger 214 can protrude above a proximal surface 200p of the coupling device 200 and a second engagement portion 222d of the trigger can protrude below a distal surface 200d of the coupling device. Accordingly, the trigger 214 can be automatically actuated upon insertion of an instrument into the coupling device 200, regardless of whether the instrument is loaded into a proximal end or a distal end of the coupling device. The trigger spring 220 can bias the trigger 214 to a neutral or resting position, such that proximal or distal deflection of the trigger along the axis A2 loads the trigger spring. As shown in FIGS. 9A-9B, the first engagement portion 222p of the trigger 214 can be defined by a proximally-extending arm formed integrally with the trigger spring 220 and the second engagement portion 222d of the trigger can be defined by a distally-extending arm formed integrally with the trigger spring. The first and second engagements portions 222p, 222d can extend in opposite directions from one another along the axis A2.

Figure 10A:
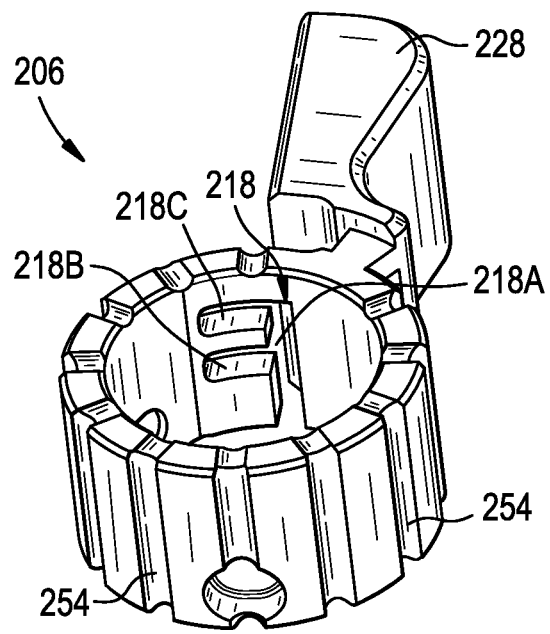
FIG. 10A is a perspective view of a clamp of the coupling device of FIG. 8A.
Figure 10B:
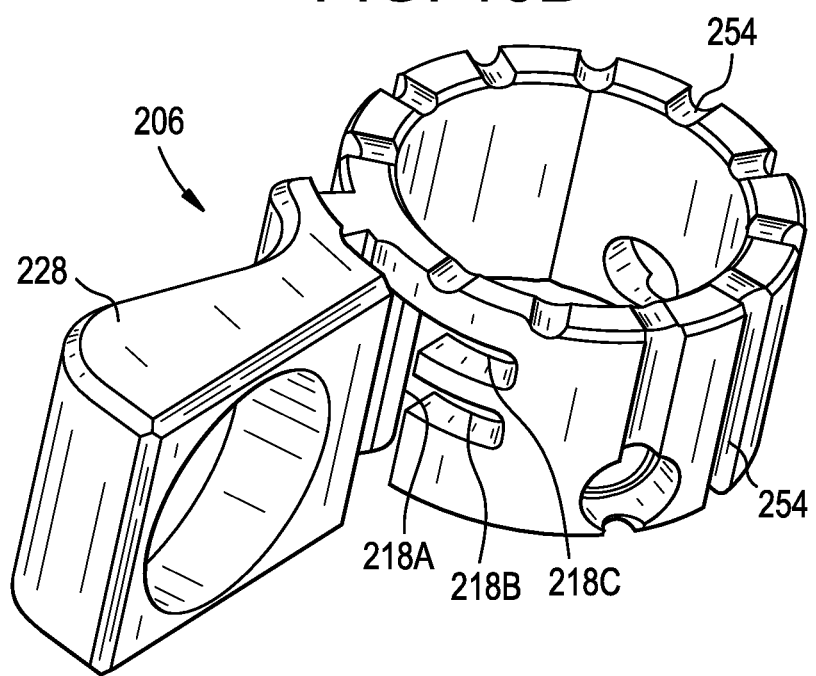
FIG. 10B is another perspective view of the clamp of FIG. 10A.

The slot 218 formed in the clamp 206 can include an axial portion 218A and first and second lateral portions 218B, 218C. As shown in FIGS. 10A-10B, the first and second lateral portions 218B, 218C can extend parallel to one another and perpendicular to the axial portion 218A. The first and second lateral portions 218B, 218C can be spaced a distance apart from one another along the axis A1. The first lateral portion 218B can be disposed distal to the axial portion 218A of the slot 218. The second lateral portion 218C can be disposed proximal to the axial portion 218A of the slot 218. The trigger spring 220 can bias the trigger 214 towards a resting position in which the rotation stop 216 is disposed in the axial portion 218A of the slot, intermediate the first and second lateral portions 218B, 218C along the axis A1.

In use, an instrument can be loaded into the proximal end of the coupling device 200 or into the distal end of the coupling device.

Figure 11A:
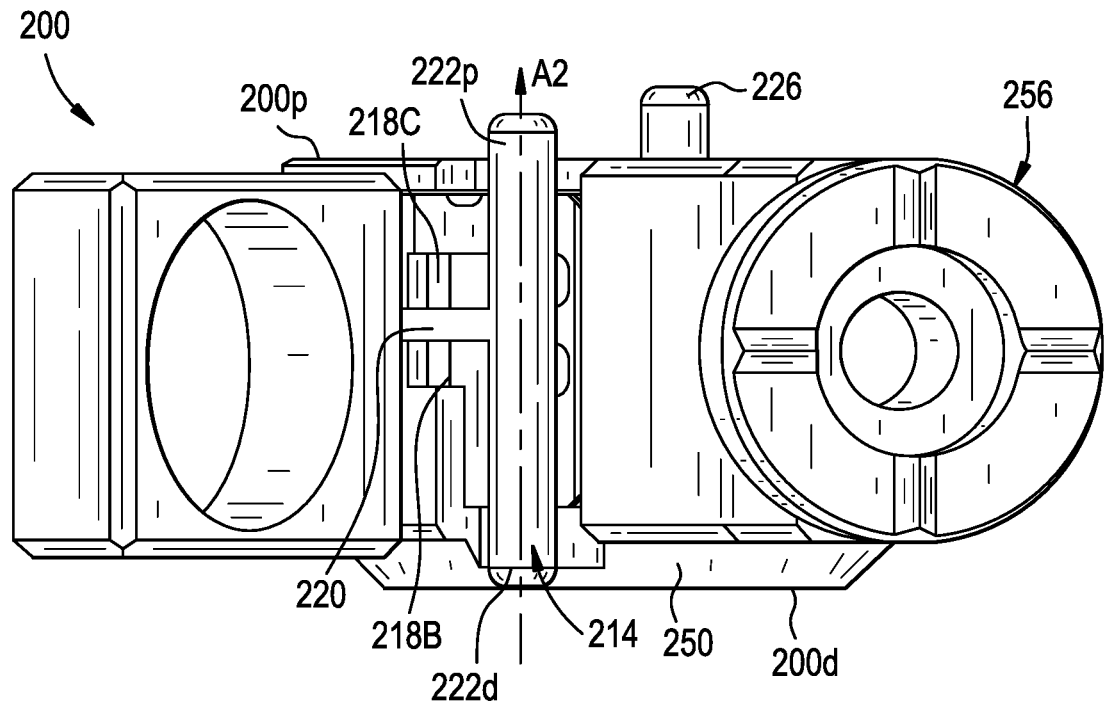
FIG. 11A is a side view of the coupling device of FIG. 8A.
Figure 11B:
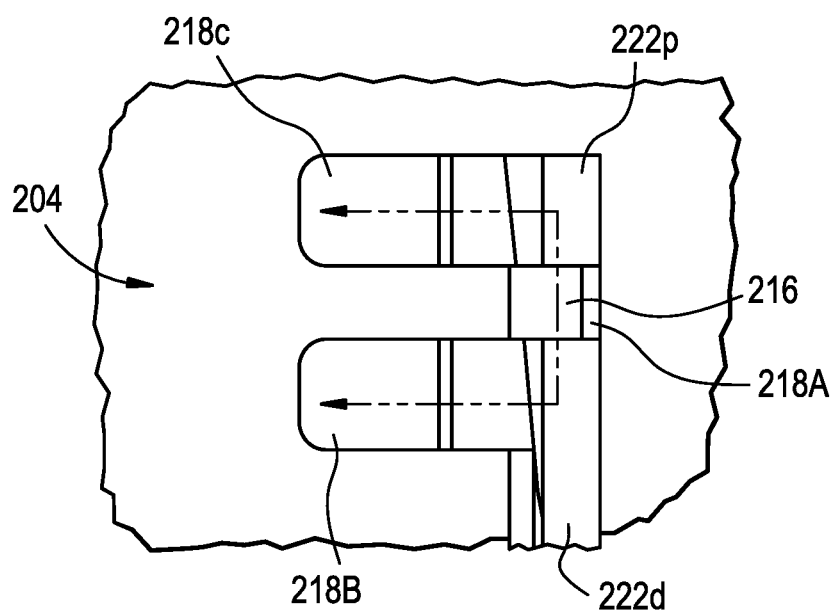
FIG. 11B is a detail side view of the coupling device of FIG. 8A, schematically illustrating movement of a rotation stop upon proximal or distal loading of an instrument.

As shown in FIGS. 11A-11B, when an instrument is loaded into the proximal end of the coupling device 200, the instrument can contact the first engagement portion 222p of the trigger 214 to displace the trigger distally along the axis A2, moving the rotation stop 216 out of the axial portion 218A of the slot 218 and into alignment with the first lateral portion 218B of the slot. In this position, the rotation stop 216 can be free to travel along the slot 218B such that the rotation stop no longer constrains rotation of the clamp 206 and therefore the clamp is free to rotate relative to the housing 204 under the bias of the clamp spring 224. The clamp 206 can then rotate relative to the housing 204 about the axis A1 to move the clamping elements 210 radially-inward to clamp onto the instrument. When the coupling device 200 is reset and the instrument removed therefrom, the trigger spring 220 can return the rotation stop 216 to the axial portion 218A of the slot 218 to once again hold the coupling device in the open position.

When an instrument is loaded into the distal end of the coupling device 200, the instrument can contact the second engagement portion 222d of the trigger 214 to displace the trigger proximally along the axis A2, moving the rotation stop 216 out of the axial portion 218A of the slot 218 and into alignment with the second lateral portion 218C of the slot. In this position, the rotation stop 216 can be free to travel along the slot 218C such that the rotation stop no longer constrains rotation of the clamp 206 and therefore the clamp is free to rotate relative to the housing 204 under the bias of the clamp spring 224. The clamp 206 can then rotate relative to the housing 204 about the axis A1 to move the clamping elements 210 radially-inward to clamp onto the instrument. When the coupling device 200 is reset and the instrument removed therefrom, the trigger spring 220 can return the rotation stop 216 to the axial portion 218A of the slot 218 to once again hold the coupling device in the open position.

The coupling device 200 can be configured to mate with the instrument differently depending on whether the instrument is loaded into the proximal end or the distal end of the coupling device.

For example, in the illustrated embodiment, only the proximal end of the coupling device 200 includes an orientation feature 226. Accordingly, an instrument loaded into the proximal end of the coupling device 200 can be constrained to one or more discrete rotational positions about the axis A1 relative to the coupling device, as defined by the orientation feature 226, whereas an instrument loaded into the distal end of the coupling device can be clamped in any of an infinite number of rotational positions about the axis A1 relative to the coupling device, or can be free to rotate relative to the coupling device after clamping. In some embodiments, only the distal end of the coupling device includes an orientation feature. In some embodiments, both the proximal and distal ends of the coupling device include an orientation feature. In some embodiments, the proximal and distal ends of the coupling device can include orientation features that differ from one another. In some embodiments, neither the proximal end nor the distal end of the coupling device includes an orientation feature.

As another example, in the illustrated embodiment, only the distal end of the coupling device 200 includes a security feature 250. Accordingly, an instrument loaded into the distal end of the coupling device 200 can be secured by the security feature 250, whereas an instrument loaded into the proximal end of the coupling device is not secured by a security feature. The security feature 250 can include a ramped, curved, stepped, or otherwise tapered protrusion formed on a surface of the coupling device 200 configured to contact an instrument inserted through the coupling device. For example, a conical ring-shaped protrusion 250 can be formed on the distal surface 200d of the coupling device 200 as shown. The conical protrusion 250 can taper radially-inward in a proximal-to-distal direction. The security feature 250 can engage with a counterpart security feature of an instrument to help center the instrument within the coupling device 200. The security feature 250 can also help ensure that an instrument is loaded into the coupling device 200 in the proper orientation, e.g., by preventing the trigger 214 from being actuated unless the instrument is inserted in an orientation in which the security feature 250 is received within a counterpart security feature of the instrument. In some embodiments, only the proximal end of the coupling device includes a security feature. In some embodiments, both the proximal and distal ends of the coupling device include a security feature. In some embodiments, the proximal and distal ends of the coupling device can include security features that differ from one another. In some embodiments, neither the proximal end nor the distal end of the coupling device includes a security feature.

The coupling device 200 can include various features to facilitate cleaning or sterilization of the coupling device. For example, the coupling device 200 can include one or more passages or lumens through which a flowable cleaning or sterilization fluid can travel to reach the inner components of the coupling device. As shown in FIG. 9A, the housing 204 can include a circumferential slit 252. The slit 252 can be open to an exterior of the coupling device 200 and can be in fluid communication with one or more of the cavities 234 of the housing 204. Accordingly, cleaning or sterilization fluid can flow through the slit 252 to the cavities 234 and the clamping elements 210 disposed therein. While a circumferential slit 252 is shown, it will be appreciated that the slit can have other shapes and can extend in other directions. As shown in FIG. 10A, the clamp 206 can include one or more axial grooves 254. The grooves 254 can be formed in an exterior sidewall of the clamp 206. The grooves 254 can extend across proximal and/or distal surfaces of the clamp 206. The grooves 254 can be in fluid communication with the clearance space between the exterior of the clamp 206 and the interior of the housing 204. The grooves 254 can be in fluid communication with the cavities 234 in which the clamping elements 210 are disposed. Accordingly, cleaning or sterilization fluid can flow through the grooves 254 to the clamp/housing interface and/or into the cavities 234 and the clamping elements 210. While axial grooves 254 are shown, it will be appreciated that the grooves can have other shapes and can extend in other directions.

As noted above, a navigation array or other component can be attached to any portion of the coupling device. For example, a navigation array 12 can be coupled to one of the handle levers 228, 230, or anywhere on the housing 204 of the coupling device 200. In the illustrated example, the handle lever 230 of the housing 204 includes a beam formed integrally therewith to which the navigation array can be attached or with which the navigation array can be integrally-formed. The beam can include a mating feature 256 for coupling the navigation array thereto. In some embodiments, the mating feature 256 can be formed on the handle 228 instead or in addition. The mating feature 256 can include any of a variety of commercially-available or industry-standard mating features.

Figure 8C:
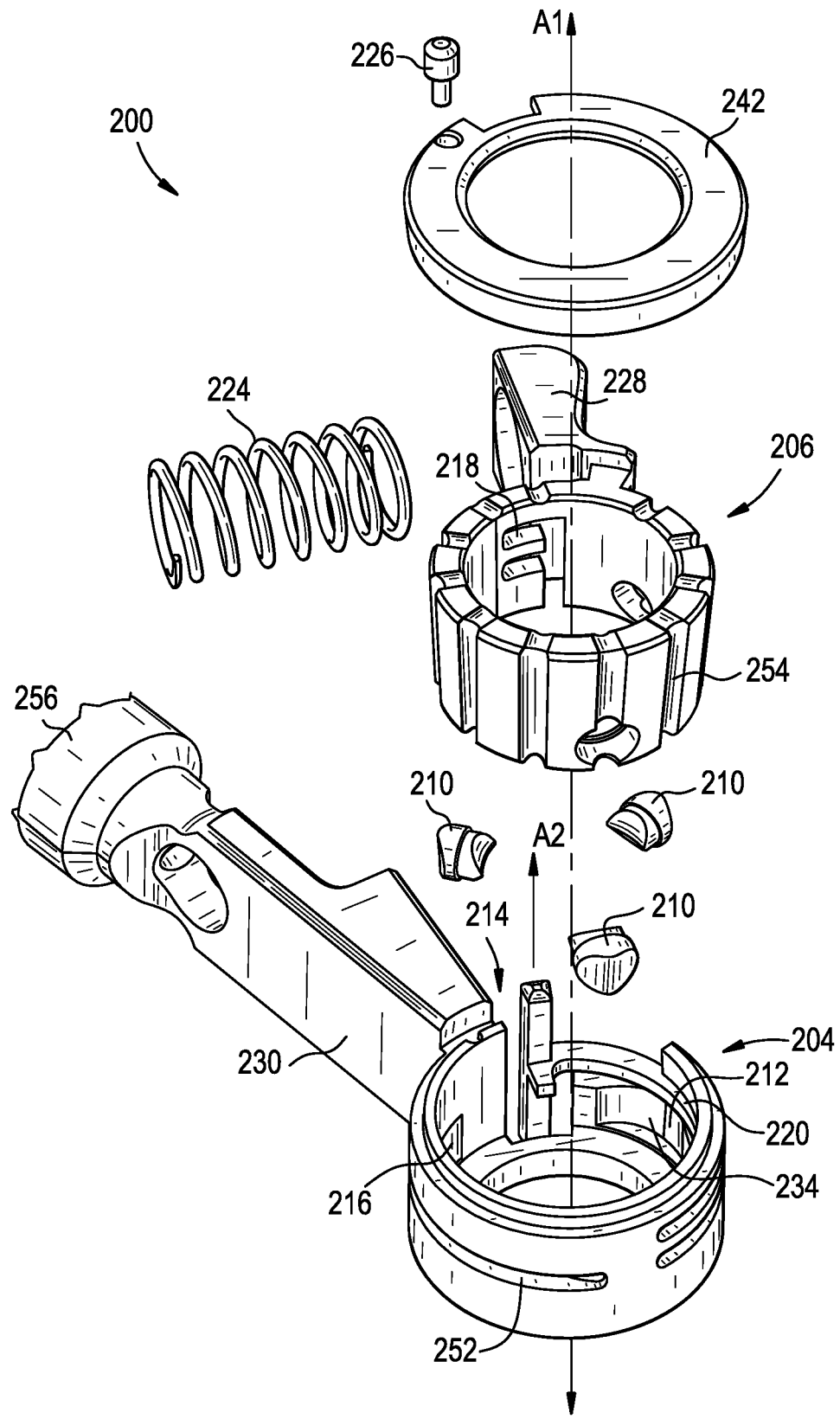
FIG. 8C is an exploded perspective view of the coupling device of FIG. 8A.
Figure 12A:
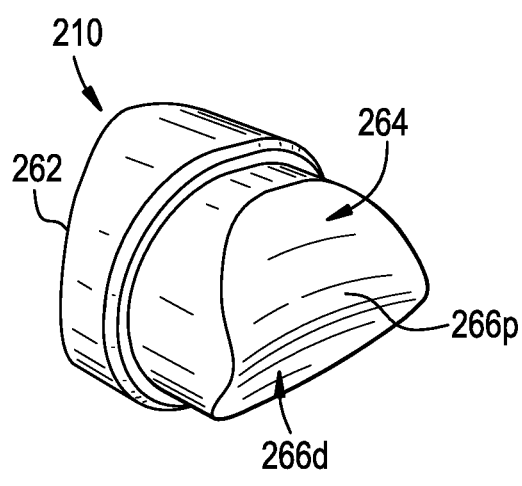
FIG. 12A is a perspective view of a clamping element of the coupling device of FIG. 8A.
Figure 12B:
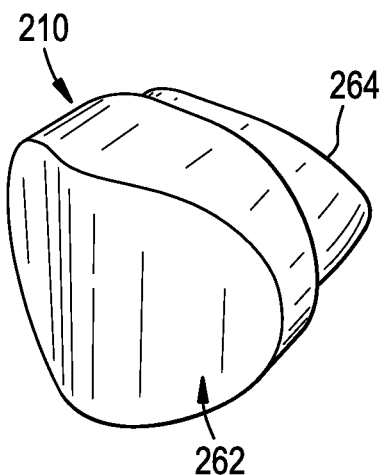
FIG. 12B is another perspective view of the clamping element of FIG. 12A.

As noted above, the coupling devices disclosed herein can include various types of clamping elements. As shown in FIGS. 8C and 12A-12B, the coupling device 200 can include wedge-shaped clamping elements 210. The clamping elements 210 can include a housing bearing surface 262 configured to contact and bear against the surface features 212 of the housing 204 and an instrument bearing surface 264 configured to contact and bear against an instrument received within the coupling device 200. The housing bearing surface 262 can include first and second planar sections that meet at a central convex portion and that extend obliquely from a plane that is tangent to the convex portion and parallel to the axis A1. The housing bearing surface 262 can interact with the surface features 212 of the housing 204 to facilitate ramping and to move the wedge 210 radially-inward during clamp actuation. The instrument bearing surface 264 can include first and second spherical sections 266p, 266d that meet at a central convex portion. The first spherical section 266p can taper radially-inward towards the convex portion in a proximal-to-distal direction. The second spherical section 266d can taper radially-inward towards the convex portion in a distal-to-proximal direction. The instrument bearing surface 264 can interact with a groove of an instrument mating geometry to center the instrument within the coupling device 200 and to push or pull the instrument axially within the coupling device to firmly seat the instrument against the proximal or distal surface 200p, 200d of the coupling device.

Figure 13A:
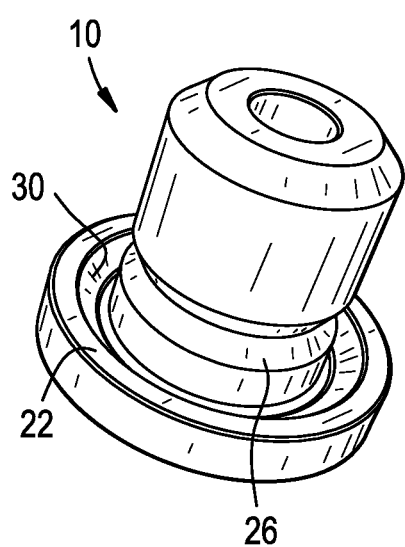
FIG. 13A is a perspective view of an instrument that can be used with the coupling device of FIG. 8A.
Figure 13B:
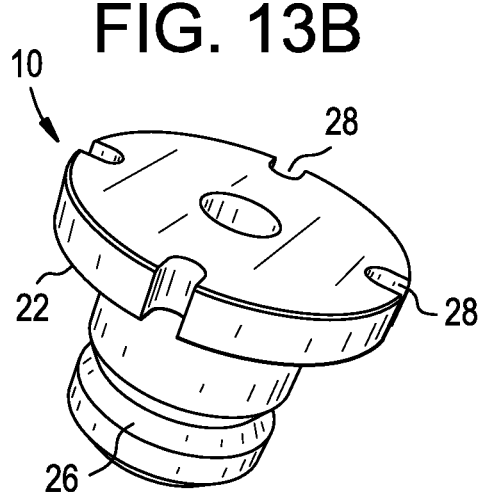
FIG. 13B is a perspective view of another instrument that can be used with the coupling device of FIG. 8A.

The coupling device 200 can be used with any of a variety of instruments. In some embodiments, one or more instruments can include a mating geometry designed to operate with the coupling device 200. Exemplary instrument mating geometries are shown in FIGS. 13A-13B. It will be appreciated that the illustrated geometries are exemplary and that the coupling device 200 can be used with any of a variety of instruments having any of a variety of mating geometries. In some embodiments, the mating geometry of the instrument can be a cylindrical shaft. In some embodiments, the mating geometry of the instrument can be a cylindrical shaft with an annular groove formed therein.

As shown in FIG. 13A, an instrument 10 can include mating geometry designed for distal loading into the coupling device 200. The mating geometry can include a conical depression 30 for mating with the security feature 250 of the coupling device 200 and a circumferential groove 26 for receiving the clamping elements 210 of the coupling device. The circumferential groove 26 can extend around an entire periphery of the instrument 10 as shown, or only in discrete positions aligned with the clamping elements 210 of the coupling device 200. The proximal and distal surfaces of the groove 26 can be curved, ramped, stepped, or otherwise tapered to facilitate axial translation of the instrument 10 relative to the coupling device 200 as the clamping elements 210 are urged radially-inward into contact with the groove. The mating geometry can include a proximal-facing contact surface 22 configured to automatically actuate the trigger 214 when the instrument 10 is loaded into the coupling device 200.

As shown in FIG. 13B, an instrument 10 can include mating geometry designed for proximal loading into the coupling device 200. The mating geometry can include an orientation feature, e.g., in the form of one or more recesses 28, for mating with the orientation feature 226 of the coupling device 200 and a circumferential groove 26 for receiving the clamping elements 210 of the coupling device. The circumferential groove 26 can extend around an entire periphery of the instrument 10 as shown, or only in discrete positions aligned with the clamping elements 210 of the coupling device 200. The proximal and distal surfaces of the groove 26 can be curved, ramped, stepped, or otherwise tapered to facilitate axial translation of the instrument 10 relative to the coupling device 200 as the clamping elements 210 are urged radially-inward into contact with the groove. The mating geometry can include a distal-facing contact surface 22 configured to automatically actuate the trigger 214 when the instrument 10 is loaded into the coupling device 200.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A method of attaching an instrument to a coupling device, comprising:
   inserting a portion of the instrument into an instrument channel of the coupling device, thereby displacing a trigger of the coupling device to release a clamp of the coupling device; and
   rotating the clamp within a housing of the coupling device to cause one or more clamping elements of the clamp to move radially-inward to clamp the instrument.

2. The method of claim 1, wherein said displacing of the trigger and said rotating of the clamp occur automatically upon said insertion of the instrument.

3. The method of claim 1, wherein the instrument is loaded into a proximal end of the coupling device to displace the trigger distally.

4. The method of claim 1, wherein the instrument is loaded into a distal end of the coupling device to displace the trigger proximally.

5. The method of claim 1, wherein displacing the trigger comprises moving a rotation stop of the trigger out of an axial portion of a slot formed in the clamp and into a lateral portion of the slot.

6. The method of claim 1, wherein rotating the clamp comprises carrying the clamping elements across a surface feature of the housing to urge the clamping elements radially-inward.

7. The method of claim 1, wherein the trigger is displaced relative to the housing along an axis that is parallel or substantially parallel to a central longitudinal axis of the instrument channel.

8. The method of claim 1, wherein clamping the instrument comprises radially centering the instrument in the instrument channel and translating the instrument axially within the instrument channel to urge an abutment surface of the instrument against a counterpart surface of the coupling device.

9. The method of claim 1, wherein an orientation feature of the coupling device prevents the instrument from being inserted far enough into the coupling device to displace the trigger and release the clamp until the orientation feature of the coupling device is aligned with an orientation feature of the instrument.

10. The method of claim 1, wherein displacing the trigger loads a flexible beam to which the trigger is mounted to bias the trigger against said displacement.

11. The method of claim 1, wherein the coupling device has a navigation array attached thereto such that the instrument attaches to the navigation array via the clamp.

12. A method of coupling, comprising:
    inserting an instrument into a coupling device along a first axis, the coupling device having a housing and a clamp that move relative to one another to couple the coupling device to the instrument;
    actuating the clamp of the coupling device by displacing a trigger coupled to the clamp from a first position relative to the clamp to a second position relative to the clamp; and
    engaging the instrument within the clamp to retain the device within the coupling device.

13. The method of claim 12, wherein the coupling device includes one or more devices attached thereto prior to the instrument being inserted therethrough, wherein the instrument and the one or more devices are attached to one another via the coupling.

14. The method of claim 12, wherein a rotation stop of the trigger engages an axially extending slot of the housing in the first position such that the clamp cannot move relative to the housing, and a longitudinally extending slot of the housing in the second position such that the clamp is free to move relative to the housing.

15. The method of claim 12, wherein actuating the clamp occurs substantially automatically upon insertion of the instrument into the coupling device.

16. The method of claim 12, wherein the trigger moves along an axis parallel to the first axis.

17. The method of claim 12, wherein the instrument contacts an engagement portion of the trigger to actuate the clamp.

18. The method of claim 12, wherein actuating the clamp further comprises rotating the clamp relative to the housing to engage the instrument in a channel thereof.

19. The method of claim 12, wherein movement of the clamp from the first position to the second position causes one or more clamping elements of the clamp to move radially-inward into the channel to clamp the instrument thereto.

20. The method of claim 12, wherein the one or more clamping elements are wedged between the instrument and the housing when retaining the instrument within the coupling device.

* * * * *